US006974436B1

(12) United States Patent
Aboul-Hosn et al.

(10) Patent No.: US 6,974,436 B1
(45) Date of Patent: *Dec. 13, 2005

(54) INTEGRATED PUMP AND CANNULA SYSTEM AND RELATED METHODS

(75) Inventors: Walid N. Aboul-Hosn, Fair Oaks, CA (US); William R. Kanz, Sacramento, CA (US); James W. Cartwright, Sacramento, CA (US); Damien Shulock, Sacramento, CA (US); Kelly J. McCrystle, Sacramento, CA (US)

(73) Assignee: A-Med Systems, Inc., W. Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/889,442

(22) PCT Filed: Jan. 14, 2000

(86) PCT No.: PCT/US00/01095

§ 371 (c)(1),
(2), (4) Date: Dec. 9, 2002

(87) PCT Pub. No.: WO01/78807

PCT Pub. Date: Oct. 25, 2001

Related U.S. Application Data

(63) Continuation-in-part of application No. 09/462,656, filed on Jan. 14, 2000, which is a continuation-in-part of application No. 08/933,566, filed on Sep. 19, 1997, now Pat. No. 6,083,260.

(51) Int. Cl.[7] .......................... A61M 5/00; A61M 3/00; A61M 25/16; A61M 1/10; A61B 18/18

(52) U.S. Cl. ...................... 604/9; 604/43; 604/537; 604/264; 623/3.13; 623/3.26; 606/16

(58) Field of Search .................. 604/8, 9, 27–28, 604/30, 43, 48, 93.01, 131, 151, 164.11, 170.03, 604/247, 264, 4.01, 6.11, 523, 532, 533, 537, 604/539; 600/16–18; 623/3.1, 3.13, 3.26–3.28, 623/3.15; 415/900; 417/244, 254.56

(56) References Cited

U.S. PATENT DOCUMENTS

| 4,955,856 | A | | 9/1990 | Phillips |
| 5,376,114 | A | * | 12/1994 | Jarvik .......................... 623/3.3 |
| 5,741,234 | A | | 4/1998 | Aboul-Hosn |
| 5,776,190 | A | | 7/1998 | Jarvik |
| 5,851,174 | A | | 12/1998 | Jarvik et al. |
| 6,083,260 | A | * | 7/2000 | Aboul-Hosn ................ 623/3.14 |
| 6,086,570 | A | | 7/2000 | Aboul-Hosn et al. |

(Continued)

FOREIGN PATENT DOCUMENTS

WO    WO 99/02204    1/1999

(Continued)

*Primary Examiner*—Patricia Bianco
(74) *Attorney, Agent, or Firm*—Ryan Kromholz & Manion, S.C.

(57) ABSTRACT

The present invention relates to systems and methods for transporting fluid between different locations within a body cavity and, in one particular application, systems and methods for transporting fluids to maintain at least partial blood flow through a protected blood flow path within the right and/or left side of the heart during surgery. The protected blood flow path may be established by positioning one or more conduits within at least a portion of the right and/or left sides(s) of the heart. At least partial blood flow may be maintained through the protected blood flow path by the pumping action of a blood pump disposed within the conduit.

9 Claims, 18 Drawing Sheets

U.S. PATENT DOCUMENTS

| | | |
|---|---|---|
| 6,113,536 A | 9/2000 | Aboul-Hosn et al. |
| 6,123,725 A * | 9/2000 | Aboul-Hosn ............... 623/3.25 |
| 6,152,704 A | 11/2000 | Aboul-Hosn et al. |
| 6,186,981 B1 * | 2/2001 | Cho ........................... 604/117 |
| 6,210,133 B1 | 4/2001 | Aboul-Hosn et al. |
| 6,210,397 B1 | 4/2001 | Aboul-Hosn et al. |
| 6,228,063 B1 | 5/2001 | Aboul-Hosn |
| 6,234,960 B1 | 5/2001 | Aboul-Hosn et al. |
| 6,287,319 B1 | 9/2001 | Aboul-Hosn et al. |
| 6,295,877 B1 | 10/2001 | Aboul-Hosn et al. |
| 6,395,026 B1 * | 5/2002 | Aboul-Hosn et al. ...... 623/3.13 |
| 6,532,964 B2 | 3/2003 | Aboul-Hosn et al. |
| 2003/0023201 A1 | 1/2003 | Aboul-Hosn et al. |
| 2003/0205233 A1 | 11/2003 | Aboul-Hosn et al. |

FOREIGN PATENT DOCUMENTS

| | | |
|---|---|---|
| WO | WO 99/65546 | 12/1999 |
| WO | WO 00/12148 | 3/2000 |
| WO | WO 00/18448 | 4/2000 |
| WO | WO 00/19097 | 4/2000 |
| WO | WO 00/69489 | 11/2000 |

* cited by examiner

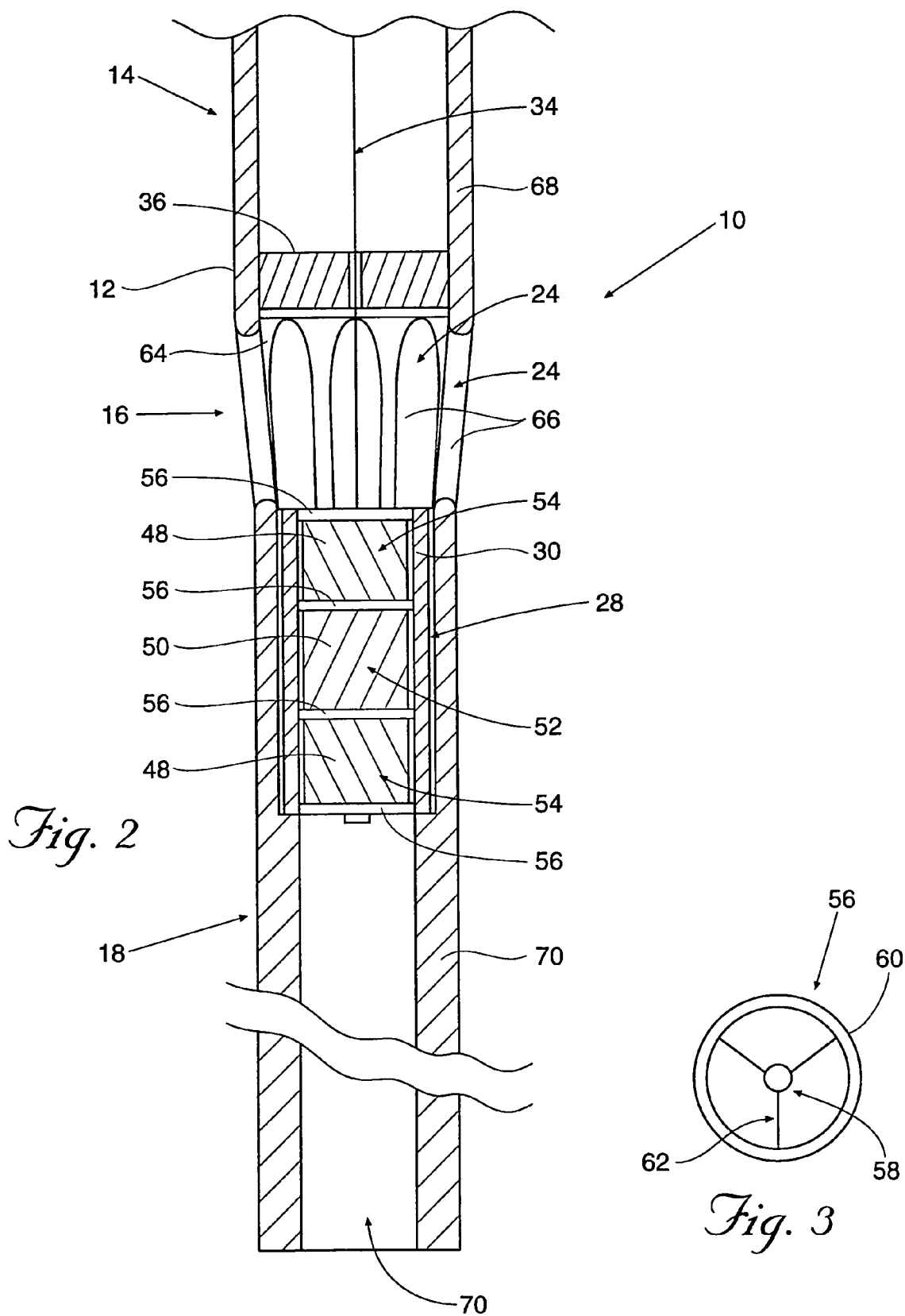

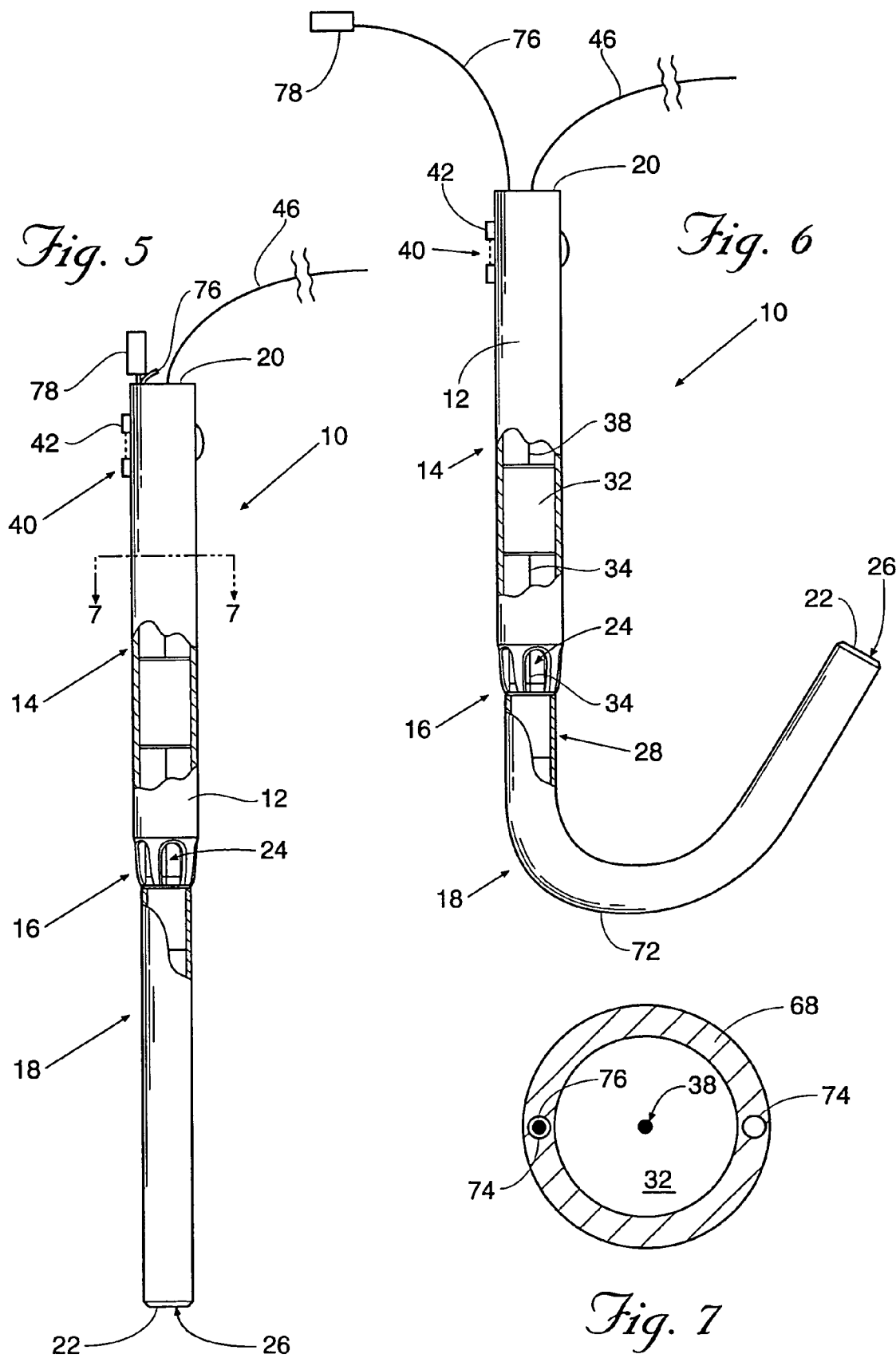

INTEGRATED PUMP AND CANNULA SYSTEM AND RELATED METHODS

REFERENCE TO RELATED APPLICATIONS

This application is a continuation-in-part of U.S. patent application Ser. No. 09/462,656, filed Jan. 14, 2000, entitled "Transport Pump and Organ Stabilization Apparatus Including Related Methods," which is a continuation-in-part of U.S. patent application Ser. No. 08/933,566, filed Sep. 19, 1997, now U.S. Pat. No. 6,083,260.

BACKGROUND OF THE INVENTION

I. Field of the Invention

The present invention involves systems and methods for transporting fluids between various locations in the body, such as during surgical procedures. More particularly, the present invention is directed to a cannula arrangement having an integrated pump disposed therein for transporting blood between various points in the heart to provide right and/or left heart support cardiac surgery.

II. Discussion of the Prior Art

During most surgical procedures, bodily fluids are directed and transferred to various locations with the assistance of artificial pumping apparatus. Major heart surgery, for example, is oftentimes accomplished by procedures that require full cardiopulmonary bypass (CPB) through the use of artificial heart-lung machines and complete cessation of cardiopulmonary activity. While the average mortality rate with this type of procedure is low, it is nonetheless associated with a complication rate that is often much higher compared to when cessation of the heart and CPB are not required. The use of CPB continues to represent a major assault on a host of body systems. For example, there is noticeable degradation of mental faculties following such surgeries in a significant percentage of patients who undergo coronary artery bypass grafting (CABG) procedures. The CABG procedure generally involves open chest surgical techniques to treat diseased vessels. During this procedure, the sternum of the patient is cut in order to spread the chest apart and provide access to the heart. During surgery the heart is stopped, and by the use of CPB blood is diverted from the lungs to an artificial oxygenator. In general CABG procedures, a source of arterial blood is then connected to a coronary artery downstream from the occlusion. The source of blood is often an internal mammary artery, and the target coronary artery is typically among the anterior or posterior arteries which may be narrowed or occluded. The degradation of mental faculties resulting from CABG procedures is commonly attributed to cerebral arterial blockage and emboli from debris in the blood generated by the use of CPB. At the same time, the dramatic increase in the life expectancy of the general population has resulted in patients that are more likely to be older and in poor health, with less cardiovascular, systemic, and neurologic reserve needed to recover from the trauma caused by the use of CPB. As a consequence, inflammatory, hemostatic, endocrinologic, and neurologic stresses are tolerated to a much lesser degree by a significant number of patients today, and play a more significant role in CPB-induced morbidity.

The combined statistics of postoperative morbidity and mortality continue to illustrate the shortcomings of CPB. The extracorporeal shunting and artificially induced oxygenation of blood activates a system wide roster of plasma proteins and blood components in the body including those that were designed to act locally in response to infection or injury. When these potent actors are disseminated throughout the body without normal regulatory controls, the entire body becomes a virtual battleground. The adverse hemostatic consequences of CPB also include prolonged and potentially excessive bleeding. CPB-induced platelet activation, adhesion, and aggregation also contribute to a depletion in platelet number, and is further compounded by the reversibly depressed functioning of platelets remaining in circulation. The coagulation and fibrinolytic systems both contribute to hemostatic disturbances during and following CPB. However, the leading cause of morbidity and disability following cardiac surgery is cerebral complications. Gaseous and solid micro and macro emboli, and less often perioperative cerebral hypoperfusion, produce neurologic effects ranging from subtle neuropsychologic deficits to fatal stroke. Advances in computed tomography, magnetic resonance imaging, ultrasound, and other imaging and diagnostic techniques have added to the understanding of these complications. But with the possible exception of perioperative electroencephalography, these technologies do not yet permit real time surgical adjustments that are capable of preventing emboli or strokes in the making. Doppler and ultrasound evaluation of the carotid artery and ascending aorta, and other diagnostic measures, can help identify surgical patients at elevated risk for stroke and are among the growing list of pharmacologic and procedural measures for reducing that risk.

CPB also affects various endocrine systems, including the thyroid gland, adrenal medulla and cortex, pituitary gland, pancreas, and parathyroid gland. These systems are markedly affected not only by inflammatory processes, but also by physical and biochemical stresses imposed by extracorporeal perfusion. Most notably, CPB is now clearly understood to induce euthyroid-sick syndrome which is marked by profoundly depressed triiodothyronine levels persisting for days following cardiothoracic surgery. The efficacy of hormone replacement regimens to counteract this effect are currently undergoing clinical investigation. By contrast, levels of the stress hormones epinephrine, norepinephrine, and cortisol are markedly elevated during and following CPB, and hyperglycemia is also possible.

Beating heart bypass surgery has been recognized as desirable because it has the possibility of avoiding the necessity of placing the patient on a full CPB system. However, attempts at beating heart bypass surgery have met with limited success and have essentially been limited to surgery on the anterior heart vessels due to problems which develop when the beating heart is lifted or displaced from its normal position in order to perform the beating heart surgery. Typically when the beating heart is lifted or manipulated in order to provide surgical access to posterior heart vessels, a number of difficulties are encountered. When the beating heart is lifted and manipulated, the right side of the heart tends to collapse, particularly the right auricle or atrium and frequently the right ventricle and/or pulmonary artery. When the right side of the heart collapses, pulmonary blood flow either ceases or becomes inadequate, thus forcing the use of CPB. Another difficulty encountered is that, even if the right side of the heart does not collapse, the pulmonary artery and/or the pulmonary vein frequently become crimped or kinked thus also impeding the pulmonary blood flow. Similarly, during the lifting and manipulation of the beating heart for lateral or posterior access, the left side of the heart, particularly the left auricle or left atrium can also collapse or partially collapse, thus impeding aortic circulatory blood flow. Further, when the beating heart is lifted or manipulated for beating heart surgery access or during catheterization or cannulation procedures, the heart may lapse into arrhythmia or disrhythmia or may arrest at least a portion of the time or most of the time that the surgery is being performed thus likewise impeding pulmonary blood flow and arterial circulatory blood flow. As a result, patients undergoing beating heart surgery are at risk of having to be placed on CPB on an emergency basis in the event that the pulmonary and/or circulatory blood flow is compromised during the surgery, which presents the CPB-induced side effects previously described.

The medical community is currently performing more beating heart bypass surgery in an effort to avoid the use of full CPB. The need is increasing for apparatus systems, methods and associated equipment to enhance the capability and versatility of beating heart surgery and to avoid CPB procedures in any heart surgery. The current trend toward thoracoscopic methods of performing bypass surgery, without opening the chest cavity, have resulted in limited success and applicability primarily due to the limited number of heart vessels which can be accessed through thoracoscopic methods. A major limitation of thorascopic bypass surgery methods is due to the fact that only the anterior heart vessels are accessible for surgery. More importantly, even open chest surgery providing full access to the heart also requires CPB when bypass surgery is performed on the lateral or posterior vessels of the heart, due to the fact that in conventional procedures the heart must be stopped when it is lifted or rotated from its normal position and manipulated for surgical access to the various heart vessels.

The present invention addresses this need by providing systems and methods for transporting blood between various points in the heart to provide right and/or left heart support so as to eliminate, or at least reduce, the need for full CPB.

SUMMARY OF THE INVENTION

The present invention provides an integrated pump and cannula system that transports fluid between different regions within the body in order to support a wide variety of surgical procedures. This system finds particular utility during cardiac applications, and will be discussed in detail below within the context of transporting blood within the heart to augment or replace the blood flow of the heart itself. It is to be readily understood, however, that the integrated pump and cannula systems of the present invention may be used in a wide variety of other applications that require the transportation of fluid between different locations within the body. When employed during cardiac surgical procedures, the integrated pump and cannula systems of the present invention are particularly advantageous in that they ensure that the patient's lungs are used for blood oxygenation, thereby avoiding the need for CPB or other external blood oxygenation equipment or procedure.

The pump and cannula system of the present invention accomplishes this goal by maintaining at least partial blood flow through a protected blood flow path within the right and/or left side(s) of a heart (beating or still) to ensure sufficient pulmonary blood flow to the lungs and/or circulatory blood flow throughout the body during cardiac surgery. In reference to this invention, the "right side" of the heart refers to and includes the vena cava veins (superior and inferior), the right atrium, the right ventricle, the pulmonary artery and any combination or all thereof. The "right side" of the heart provides the pulmonary blood flow to the lungs. The "left side" of the heart refers to and includes the pulmonary veins, the left atrium, the left ventricle, the aorta and any combination or all thereof. The "left side" of the heart provides the circulatory blood flow to the body. The terms "pulmonary artery" and "pulmonary vein" include all branches thereof, and the term "aorta" includes the aortic vessels which are near the heart and are exposed or manipulated during open chest cardiac surgery or are utilized during minimally invasive cardiac surgery. As will be explained in greater detail below, in accordance with the present invention the protected blood flow path may be established by positioning one or more conduits within at least a portion of the right and/or left sides(s) of the heart, and at least partial blood flow may be maintained through the protected blood flow path by the pumping action of a blood pump disposed within the conduit.

In an important aspect, the present invention ensures sufficient pulmonary and/or circulatory blood flow during cardiac surgery regardless of any compromise in cardiac output or function experienced during cardiac surgery. Generally speaking, such compromise conditions include any situation where the cardiac output of the heart is diminished or disrupted from normal levels. This includes any and all compromise conditions that occur or result during beating heart surgery or still or stopped heart surgery. In beating heart surgery, the cardiac output of a beating heart can become compromised in a multitude of ways. For example, when the beating heart is lifted and manipulated to provide surgical access to posterior or lateral heart vessels, portions of the right and/or left side of the heart may collapse, thereby causing the pulmonary and/or circulatory blood flow to either cease or become inadequate. Even if collapse does not occur, portions of the right and/or left side of the heart may nonetheless become crimped or kinked (particularly the pulmonary artery and/or the pulmonary vein) and thereby impede or cease the pulmonary and/or circulatory blood flow during beating heart surgery. The cardiac output of the heart may also become compromised if the heart lapses even briefly into arrhythmia, disrhythmia, or arrest during beating heart surgery. Up until now, the above-identified compromise conditions place patients undergoing beating heart surgery at risk of being placed on CPB on an emergency basis in the event that the pulmonary and/or circulatory blood flow is compromised during the surgery. By maintaining at least partial blood flow through the right and/or left sides of the heart during beating heart surgery, the present invention removes this risk and thus avoids the host of adverse side-effects associated with CPB.

The present invention provides, generally speaking, a pump and cannula system for selectively augmenting or replacing the heart's natural pumping to ensure sufficient pulmonary and/or circulatory blood flow during periods when cardiac output may become compromised (including but not limited to cardiac surgery and related procedures) or when the blood flow within the heart needs to be augmented for any reason. The pump and cannula system of the present invention may take a variety of different forms. In all embodiments, the cannula is positioned to establish a protected blood flow path within a portion of the heart (across at least one valve) and the pump may be selectively operated to maintain at least partial blood flow therethrough. For right heart support, the cannula may extend through the tricuspid valve and/or pulmonary valve into the pulmonary artery. For left heart support, the cannula may extend through the bicuspid valve and/or aortic valve into the aorta. In either embodiment, the pump is disposed within the cannula to selectively transport blood past the valve(s) through which the cannula passes to augment or replace the pumping ability of the right and/or left side of the heart. The pump and cannula system may be used during open-chest procedures, or closed chest procedures through the chest wall as part of a thoracoscopic procedure. In either event, the pump and cannula system may be introduced into the heart through a single incision the wall of the right atrium, the wall of the right ventricle, the wall of the pulmonary artery, the wall of the left atrium, the wall of the left ventricle, or the wall of the aorta. The pump, being disposed within the heart itself, has priming volume of approximately zero. The pump, in all embodiments, is preferably variable output. It may be controlled automatically in response to one of a variety of appropriate parameters, including but not limited to blood pressure, blood flow, blood oxygen level, and/or blood C02 level. In another embodiment, the pump may be controlled manually (on-demand) through the use of manual controls configured as part of the integrated pump and cannula system.

In all embodiments, the pump and cannula system may be used in both the right and left sides of the heart. The pump and cannula system of the present invention is particularly useful during beating heart surgery to overcome or prevent situations where cardiac output or outflow may become compromised. As noted above, these situations may stem from, but are not necessarily limited to, instances when the heart is lifted, rotated or otherwise manipulated to access lateral or posterior blood vessels, when the heart outflow is diminished or reduced such as by a collapse, kink, or restriction in the heart chambers or in the veins or arteries, or when the heart goes into arrhythmia or malfunctions in any way during the operation. Cardiac output may also be intentionally compromised, such as during still heart or stopped heart surgery, when the heart is deliberately stopped such as by the application of cardioplegia to perform procedures such as valve surgery, internal surgery or other reason. This system is also desirable in any heart surgery procedure, even for anterior vessel bypass, when lifting or manipulating of the heart is not anticipated. This applies to both open chest and closed chest, minimally invasive, procedures.

By having this system in place before cardiac surgery begins, the present invention thus assures that is the patient will at all times during surgery have adequate pulmonary blood flow through the lungs and/or circulatory blood flow throughout the body. More importantly, it will avoid the necessity of being placed on a CPB machine in the event of an unexpected failure of the beating heart to sustain adequate pulmonary or circulatory blood flow during beating heart surgery. This allows the heart to continue to beat and provide pulmonary and circulatory blood flow to the extent it is capable, until there is a cardiac output compromise (such as by collapse, kink, arrhythmia or arrest, etc.) which decreases or stops the blood flow output by the heart. When that occurs, the pump(s) in either or both sides of the heart may be engaged to augment and/or replace the blood flow produced by the heart such that the patient's pulmonary and/or circulatory blood flows are maintained at sufficient levels to sustain them during the surgery. By having this system in place at the beginning of the beating heart surgery, even for anterior vessel surgery when no need is anticipated, it can merely be engaged or turned on to provide pump assisted blood flow if needed on an unexpected or emergency basis, thus assuring that emergency CPB procedures are avoided. Thus, this system assures that the patient's lungs are utilized for oxygenation of the blood during the entire surgical procedure, even if an unexpected compromise in blood flow occurs.

In one embodiment, the integrated pump and cannula system is provided wherein the cannula portion is adapted for insertion through at least the pulmonary valve and a sufficient length into the pulmonary artery to provide a protected blood flow path within one or more of the right atrium, right ventricle, and pulmonary artery and the pump may be selectively operated to maintain at least a partial blood flow therethrough during beating heart surgery. Access for insertion of the cannula portion is preferably through an incision in the right atrium. If the cannula is not inserted through the tricuspid valve, but only through the pulmonary valve and into the pulmonary artery, access could be through an incision in the wall of the right ventricle or reverse access can be used by entering through an incision in the wall of the pulmonary artery. Separate cannulas can be employed, i.e., one introduced through the right atrium and through the tricuspid valve but ending in the right ventricle, and a second introduced by any desired access and beginning in the right ventricle and extending through the pulmonary valve and a desired length, according to this invention, into the pulmonary artery. The pump portion of the system is adapted for intake of blood upstream of the pulmonary valve or upstream of the tricuspid valve and output of blood into the right ventricle or into the pulmonary artery during beating heart surgery.

In another embodiment, a separate pump and cannula system may be provided for the left side wherein the cannula portion is adapted for insertion through at least the aortic valve and a sufficient length into the aorta to provide a protected blood flow path within one or more of the left atrium, left ventricle, and aorta, and the pump may be selectively operated to maintain at least partial blood flow therethrough-during cardiac surgery. As indicated above for the right side, access for the left side cannula or cannulas can be from any desired upstream or downstream incision. One or two cannulas may be employed for preventing collapse of the left side. The pump portion of the system, which may have its separate cannulas, is adapted for intake of blood upstream of the aortic valve or the bicuspid valve and output of blood into the left ventricle or the aorta during beating heart surgery.

The pump and cannula systems of the present invention may be used in either the right side system or the left side system or both depending on the particular patient or procedure. Whether the cannula for pump output extends into the pulmonary artery/aorta or extends only into the respective ventricle will similarly depend on the requirements for a particular patient or procedure. In some instances, the cardiac output may be impeded due to partial compression, wrinkling or other distortion of the ventricle muscle. Although the muscle is working, it is unable to both fill the ventricle with blood and expel or pump the blood in sufficient quantity. The pump system of this invention can be used by positioning the pump cannula output end in the ventricle to fill or preload the ventricle with blood, so the heart muscle can then pump or expel the blood from the ventricle, even though the muscle is not in its normal shape or position. In this aspect of the invention, at least partial blood flow may be maintained during surgery without the necessity of the cannula extending through the pulmonary/aortic valve. The heart may be stopped by short acting drugs that which stop the heart for a short period of time, or by electrical means affecting the electrical conduction of the heart or neurological systems or by use of electrical current to paralyze the nerves responsible for heart beating. While the heart is stopped, the pump(s) will deliver 100% of the necessary pulmonary blood flow to and from the lungs and/or 100% of the necessary circulatory blood flow to and from the body without any assistance from the heart. In the event the heart is stopped, and particularly when the heart is opened (such as for valve surgery), it is preferred to provide a seal by balloon sheath cannula, clamp or otherwise to isolate the heart, or at least one side of the heart, at the inlet cannula and output cannula so that the pumped blood is directed from the vein to the artery without leakage or backflow into the heart during the procedure. This will enhance the pulmonary and/or circulatory blood flow provided by the pump in the pump and cannula system.

In one preferred embodiment, the pump and cannula system comprises a pair of concentric conduits (forming a generally coaxial dual cannula assembly), adapted for insertion into a single incision. The outer cannula includes a flow port to provide fluid access to the interior of the outer cannula. The inner cannula has the pump coupled thereto such that, when inserted into the outer cannula, the pump is disposed within the outer cannula. The pump may be driven in one direction to draw blood into the flow port of the outer cannula and into the lumen of the inner cannula for delivery out a flow port at its distal end. Depending upon the application, the pump may be driven is an opposite or reverse direction to draw blood into the flow port at the distal end of the inner cannula for delivery out the flow port of the outer cannula. According to the present invention, the flow ports of the inner and outer cannulas are positioned one either side of a heart valve to forcibly transport blood from one side to the other, such as for providing right and/or left ventricular assist.

The pump and cannula systems of the present invention may be used in conjunction with procedures involving collapsing one lung and/or partially reducing the size of the beating heart to provide additional space in the chest cavity in which the surgeon can work. In this regard, it is noted that one lung is normally sufficient to sustain the patient during surgery. In some procedures the surgeon prefers to collapse one lung to provide additional space inside the chest cavity in which to work. The integrated pump and cannula of the present invention can accommodate such a procedure while sustaining the patient on one lung throughout the surgery and avoiding a CPB machine. Likewise, it is sometimes desired by the surgeon to shrink down the heart by evacuating blood from one or more chambers of the heart, also to provide additional space within the chest cavity in which to work. The pump and cannula system of the present invention accommodates such a procedure because it can sustain adequate pulmonary and circulatory blood flow throughout the surgical procedure.

As is apparent, this invention enables the use of various combinations of the above aspects of this invention to meet the requirements of a particular patient for the successful performance of beating heart surgery while assuring that the patient's lungs (or lung) provides the oxygenated blood to sustain the patient through the surgery and that a CPB machine and procedure is avoided. Selective use of the pump and cannula systems described herein in their various configurations results in minimum invasiveness and minimum contact of the blood with apparatus in or outside the body during beating heart bypass surgery. Thus, this invention enables all beating heart surgical procedures without the use of a CPB machine by providing pump and cannula systems placed through or around the entire right side and/or through or around the entire left side to both protect the beating heart blood flow and to augment, supplement or, when necessary, temporarily replace the beating heart blood flow during the surgery. This invention thus enables various heart surgery procedures (including both beating heart and still heart surgery) to be performed without the use of CPB machines by maintaining sufficient pulmonary blood flow through the patient's lungs (or lung) and sufficient circulatory blood flow through the patient's body to sustain the patient during the surgery.

BRIEF DESCRIPTION OF THE DRAWINGS

FIG. 2 is a sectional side view illustrating the construction of the pump and portions of the cannula of the integrated pump and cannula system shown in FIG. 1;

FIG. 3 is a top view of a drive shaft support ring of the pump shown in FIG. 2;

FIGS. 5–6 are partial sectional side views illustrating the feature of temporarily straightening out the pre-formed curves in the cannula to facilitate negotiating tortuous pathways with the integrated pump and cannula system of the present invention;

FIG. 7 is a cross-sectional view taken along lines 7—7 in FIG. 6, illustrating a plurality of lumens formed in the walls of the cannula for temporarily receiving straightening members therein;

DETAILED DESCRIPTION OF THE INVENTION

Figure 1:
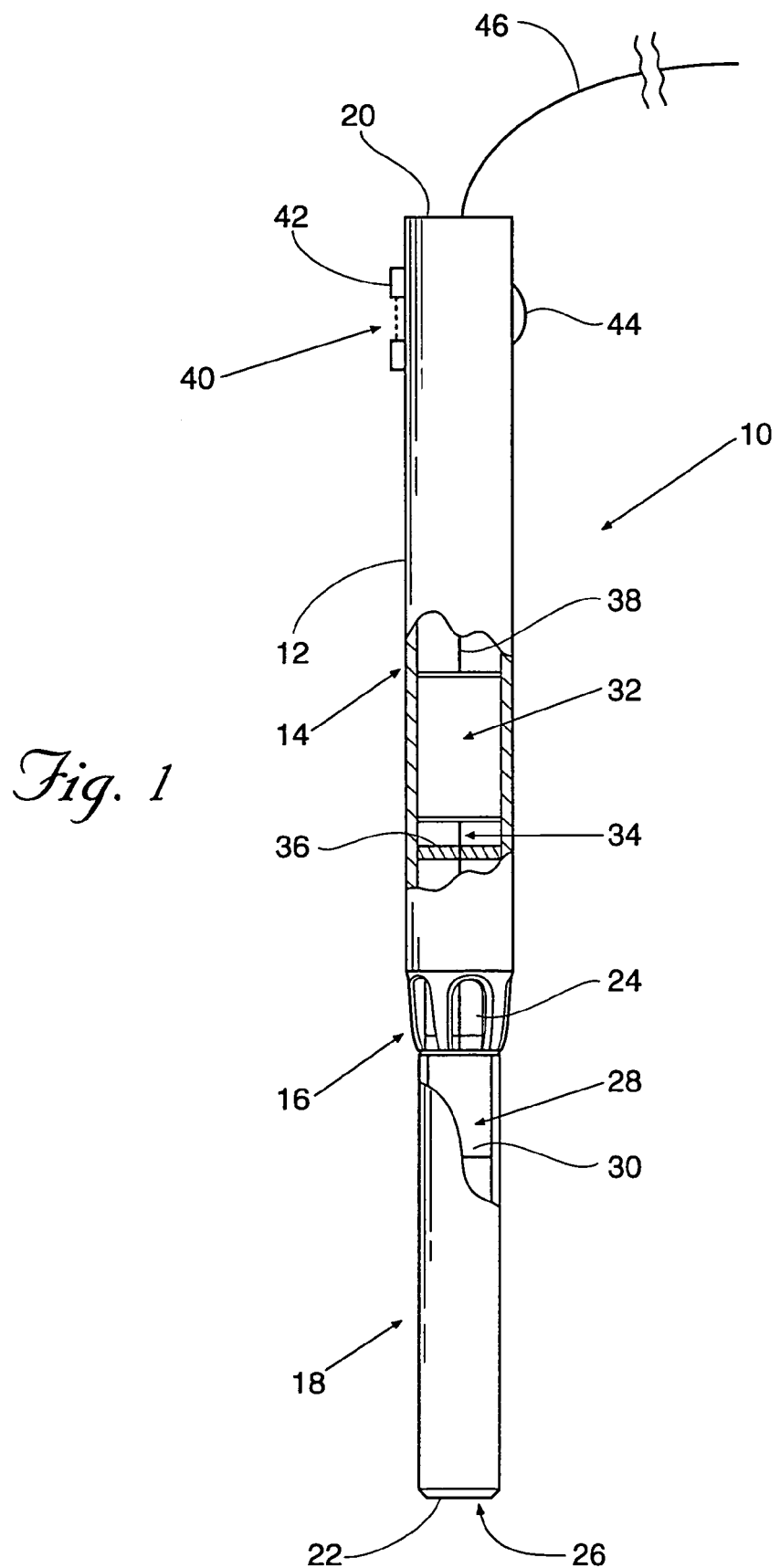
FIG. 1 is a partial sectional side view illustrating an integrated pump and cannula systems according to a first preferred embodiment of the present invention.

The present invention addresses the need to eliminate the use of CBP or other external blood oxygenation devices or procedures in cardiac surgery and related procedures. The present invention accomplishes this by providing an integrated pump and cannula system which, in use, is capable of maintaining at least partial blood flow through a protected blood flow path within the right and/or left side of the heart during surgery. The various embodiments of this system (to be described below) can be employed alone or in combination depending upon the cardiac procedure to be undertaken. The common denominator between all embodiments, however, is the combined use of at least one cannula positioned within at least a portion of the right and/or left heart to establish a protected blood flow path, and a pump disposed within the cannula to maintain at least partial blood flow through the protected blood flow path, particularly during periods when cardiac output may become compromised.

The integrated pump and cannula systems of the present invention enables safe heart surgery on anterior lateral and posterior blood vessels, in either beating heart or still heart procedures, without the necessity of using CPB. The pump and cannula systems disclosed herein can provide right heart support during beating heart surgery by pumping blood through or across the right side of the heart to augment or supplement pulmonary blood flow produced by the beating heart during surgery. If the heart temporarily collapses or lapses into arrest or disrhythmia during surgery, the supplemental pulmonary blood flow provided by the pump system of this invention eliminates the necessity of the use of CPB. Similarly, the pump and cannula system of this invention can be used with the left heart to provide sufficient supplemental arterial flow of blood to satisfy patient requirements until any compromise condition, such as heart collapse or disrhythmia, is corrected during beating heart surgery, thereby avoiding the need for CPB. By way of example only, the pump and cannula systems described below are useful in a variety of cardiac applications, including but not limited to procedures involving coronary artery bypass graft (CABG). In addition to avoiding the need for CPB, the pump and cannula systems of the present invention are also advantageous in that, by augmenting or replacing the pumping function of the right and/or left ventricle, the heart naturally decompresses (due to the reduced blood volume) which allows a greater degree of freedom to rotate and manipulate the heart for better access to target bypass vessels. This is particularly important in endoscopic surgery. While the pump and cannula systems disclosed herein are discussed primarily with respect to their usefulness in providing right and/or left heart support during beating heart surgery, it is to be readily understood that these pump and cannula systems also enable still heart surgery, such as valve or other internal heart repair, without the use of CPB.

FIG. 1 illustrates an integrated pump and cannula system 10 according to a first preferred embodiment of the present invention. The integrated pump and cannula system 10 includes a cannula 12 having a main body portion 14, an intermediate portion 16, and a distal portion 18 which are formed or bonded together to comprise a unitary element having a single lumen extending from a proximal end 20 to a distal end 22. The intermediate portion 16 includes a plurality of flow ports 24 formed therein which allow fluid (i.e. blood) to flow into and out of the distal portion 18 of the cannula 12. A single flow port 26 is formed in the end of the distal region 18 which similarly allows fluid such as blood to flow into and out of the distal portion 18. A blood pump (shown generally at 28) is disposed within the distal portion 18 of the cannula 12 near the junction with the flow ports 24. The blood pump 28 includes a generally tubular shroud member 30 which encloses a rotor (not shown). A motor 32 is disposed within the main body portion 14 of the cannula 12 for the purpose of driving the pump 28. The physical coupling between the motor 32 and the pump 28 is accomplished through the use of a drive shaft 34 which extends distally from the motor 32, through an optional hemostasis valve 38, for connection to the rotor (not shown) disposed within the shroud member 30 of the pump 28. A control wire 36 extends from the proximal side of the motor 32 for electrical connection to a control circuit (designated generally at 40) disposed near the proximal end 20 of the cannula 12. By way of example only, the control circuit 40 includes an ON-OFF switch 42, an RPM adjustment member 44, and additional control circuitry disposed within the cannula 12. The control circuitry within the cannula 12 preferably receives its power from a power cable 46 and may comprise any number of well known circuit arrangements capable of controlling the power to the motor 32 and the speed of the motor 32 to, in turn, control the operation of the pump 28. In the embodiment shown, for example, the RPM adjustment member 44 is a thumb-wheel coupled to a potentiometer element forming part of the internal control circuitry providing the ability to selectively adjust the speed (and flow rate) of the pump 28. Although not shown, an alternative embodiment may include providing a warning or communication mechanism on the cannula 12, such as a series of LED's, a small LCD panel, a numerical readout, or an audio signal to, for example, communicate warnings to the user from pressure readings obtained by pressure sensing devices disposed on or in the cannula 12.

The integrated pump and cannula system 10 of the present invention defines a fluid flow path which extends between the flow ports 24 in the intermediate portion 16 and the flow port 26 at the end of the distal portion 18. In use, the pump and cannula system 10 operates to transport fluid in one of two directions. With the pump 28 operating in a first (i.e. forward) direction, fluid will be drawn into the flow ports 24 of the intermediate portion 16 and transported through the distal portion 18 for delivery out the flow port 26. With the pump 28 operating in a second (i.e. reverse) direction, fluid will be drawn into the flow port 26 and transported through the distal portion 18 for delivery out the flow ports 24 in the intermediate portion 16. The integrated pump and cannula system 10 finds application in virtually any setting which requires the ability to transport a fluid between different locations, and particularly in surgical procedures where bodily fluids are commonly directed and transferred between various locations within the body with the assistance of artificial pumping apparatus. As will be explained in detail below, cardiac surgery represents a significant area of application for the integrated pump and cannula system 10 of the present invention in that, by maintaining at least partial blood flow within the right and/or left sides of the heart during surgery, the need for CPB during such procedures may be greatly reduced if not eliminated altogether. The system of the present invention is capable of maintaining at least partial blood flow within the right and/or left sides of the heart by inserting the pump and cannula system 10 into the right and/or left sides of the heart such that the flow ports 24 and flow port 26 are disposed on opposite sides of at least one heart valve and the pump 28 operated to transport blood therebetween. Transporting blood in this fashion operates to augment or replace the pumping ability of the heart itself, and ensures that sufficient amounts of pulmonary and/or circulatory blood flows are maintained during surgery to avoid the need for CPB.

FIG. 2 illustrates the construction of the pump 28 and portions of the cannula 12 according to an exemplary embodiment of the present invention. The pump 28 is preferably an axial pump which, in addition to the shroud member 30, includes a pair of stators 48 disposed on either side of a rotor 50. The rotor 50 is rigidly coupled to the shaft 34 so as to be rotatable within the shroud member 30. The stators 48, on the contrary, are maintained in a stationary position within the shroud member 30. The rotor 50 includes a plurality of spiral blades or vanes 52 which serve to propel fluid (i.e. blood) in an axial fashion through the pump 28. The stators 48 each include a plurality of spiral blades or vanes 54 disposed in an opposite direction as the blades 52 on the rotor 50, which vanes or blades 54 act to counter the rotational or tangential component imparted upon the blood by the rotor 50 to thereby produce a more laminar flow as it exits the pump 28. A plurality of shaft support members 56 (shown in top view in FIG. 3) are provided on both sides of each of the rotor 50 and stators 48. Each shaft support member 56 includes an inner ring 58 for accepting and supporting the drive shaft 34, an outer ring 60 disposed against the inner surface of the shroud member 30, and a plurality of struts 62 to buttress the inner ring 58 in position within the outer ring 60. Having two stators 48 positioned in either side of the rotor 50 is a preferred embodiment because the pump 28 can operate efficiently and effectively in both direction, thereby providing the ability to switch the direction of fluid flow by simply reversing the direction of rotation. However, it is to be readily understood that the axial pump 28 shown is set forth by way of example only, and that any number of well known axial flow pump designs may be used, as well as additional types of pumps, including but not limited to mixed flow pumps commonly known in the art. In similar fashion, the motor 32 may comprise any number of commercially available motors suitable for use in this environment, including but not limited to miniature electric motors, pneumatically-driven motors, etc.

As also detailed in FIG. 2, the main body portion 14, intermediate portion 16, and distal portion 18 of the cannula 12 are each generally tubular in shape and define a common lumen therewithin. The intermediate portion 16 includes a wall 64 having a plurality of apertures 66 defining the flow ports extending generally longitudinally between the proximal and distal ends of the portion 16. The main body portion 14 includes a wall 68 connected to the proximal end of the wall 64 of the intermediate portion 16. In this embodiment, the hemostasis valve 36 is disposed near the distal end of the main body portion 14 and serves to protect against the unwanted migration of blood around the drive shaft 34 and into the main body portion 14. The hemostasis valve 36 may comprise any number of commercially available hemostasis valves suitable to allow the shaft 34 to rotate without undue blood leakage into the main body portion 14. The distal portion 18 of the cannula 12 includes a wall 70 having a proximal end connected to the distal end of the wall member 64 of the intermediate portion 16, and a distal end containing flow port 26. The interior surface of distal portion wall 70 is preferably dimensioned to receive the shroud member 30 in position adjacent the intermediate flow ports 24 of the intermediate portion 16. In this arrangement, the pump 28 (under the direction of the motor 32) can draw blood in a distal direction into the flow ports 24, through the pump 28, and out the flow port 26, or alternatively, the pump 28 may be reversed to draw blood in a proximal direction into the flow port 26, through the pump 28, and out the flow ports 24 in the intermediate portion 16. As will be explained below, this may be advantageous in transporting blood within the heart in both antegrade and retrograde fashions for right and/or left heart support.

The cannula 12 (i.e. each of its constituent portions 14, 16, 18) can be formed of materials ranging from rigid to flexible, and in the preferred embodiment comprise a semi-rigid transparent material such as polyurethane or silicone having a hardness of between about 30A and 90A on a Shore durometer scale and capable of withstanding sterilization by ethylene oxide (ETO). The portions 14, 16, 18 of cannula 12 may comprise separate elements that are bonded or otherwise secured to one another to form a unitary body. The cannula 12 may also be constructed via injection molding or other known techniques to comprise a single element having the aforementioned portions 14, 16, 18 defined thereon. In either case, structural reinforcement may be provided, such as by molding or embedding spiraling wire (not shown) into the walls 68, 70, which spiraling wire may extend either partially or fully across the length of the cannula 12. As will be readily appreciated, such spiraling wire facilitates handling the cannula 12 and furthermore reduces the possibility of the distal portion 18 collapsing or being otherwise restricted or pinched shut. Other ways of reinforcing the tubular areas of the cannula 12 are known in the art and will adapt equally well to the present invention. Such reinforcement may be omitted if the cannula material is sufficiently rigid or if sufficient fluid flow is present within the cannula 12. The cannula 12 may also contain radiopaque markings (not shown) to aid in determining the placement of the cannula 12 within the patient's body using known imaging techniques.

Figure 4:
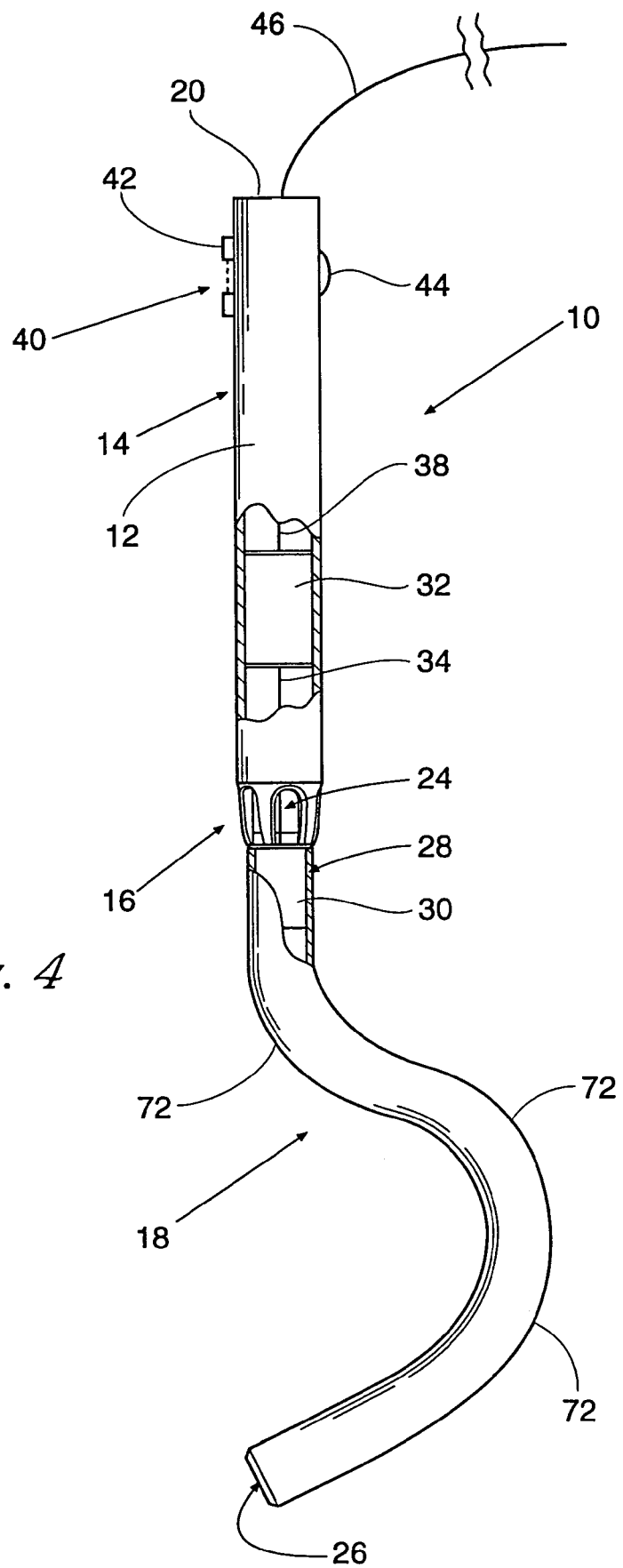
FIG. 4 is a partial sectional side view illustrating an integrated pump and cannula systems having pre-formed curve(s) formed in a distal portion of the cannula according to an embodiment of the present invention.

FIG. 4 illustrates an important aspect of the present invention, wherein the distal portion 18 of the cannula 12 may be equipped with one or more pre-formed curves 72 to facilitate cannula maneuverability during insertion in the patient's body, and more particularly the negotiation of tortuous passages within the heart. The angle of the pre-formed curve 72 may be anywhere in the range of 0–320 degrees, with the curves being disposed anywhere along the length of the distal portion 18 of cannula 12 and in any one or more distinct planes, depending on the particular application. As shown in FIGS. 5–7, the cannula 12 may optionally be equipped with a mechanism to temporarily straighten the cannula 12 to assist in placing the cannula 12 within a desired region within the heart. As shown, auxiliary lumens 74 may be provided extending longitudinally within the walls 68, 64, 70 of the cannula 12 (from the proximal end 20 to a location at or near the distal end 22) such that a straightening wire 76 or wires may be selectively introduced therein and employed to impart or relieve forces so as to induce deformation and curvature of the cannula 12. In this case, the integrated pump and cannula system 10 could be introduced into an incision in the wall of a heart chamber or passage while in the generally straight configuration shown in FIG. 5 (with a straightening wire 76 fully inserted up to the handle 78), after which point the straightening wire 76 can be removed such that the pre-formed curve takes its nature curved shape as shown in FIG. 6 to be more readily directed into the desired chamber or passage in the heart. Pre-formed curve 72 may also be of an adjustable angle, formed by expandable joints, such as through the use memory shaped material which, in the presence of current or heat, will either change length or shape depending upon the characteristics of material used. An example of such a material is Nitinol, commercially available from Educational Innovations, Inc. 151 River Road, Cos Cab CT 06807. If imbedded within the walls of the cannula 12 and activated with electrical current, Nitonol may allow an operator to selectively alter the position and orientation of the distal end 22.

Figure 8:
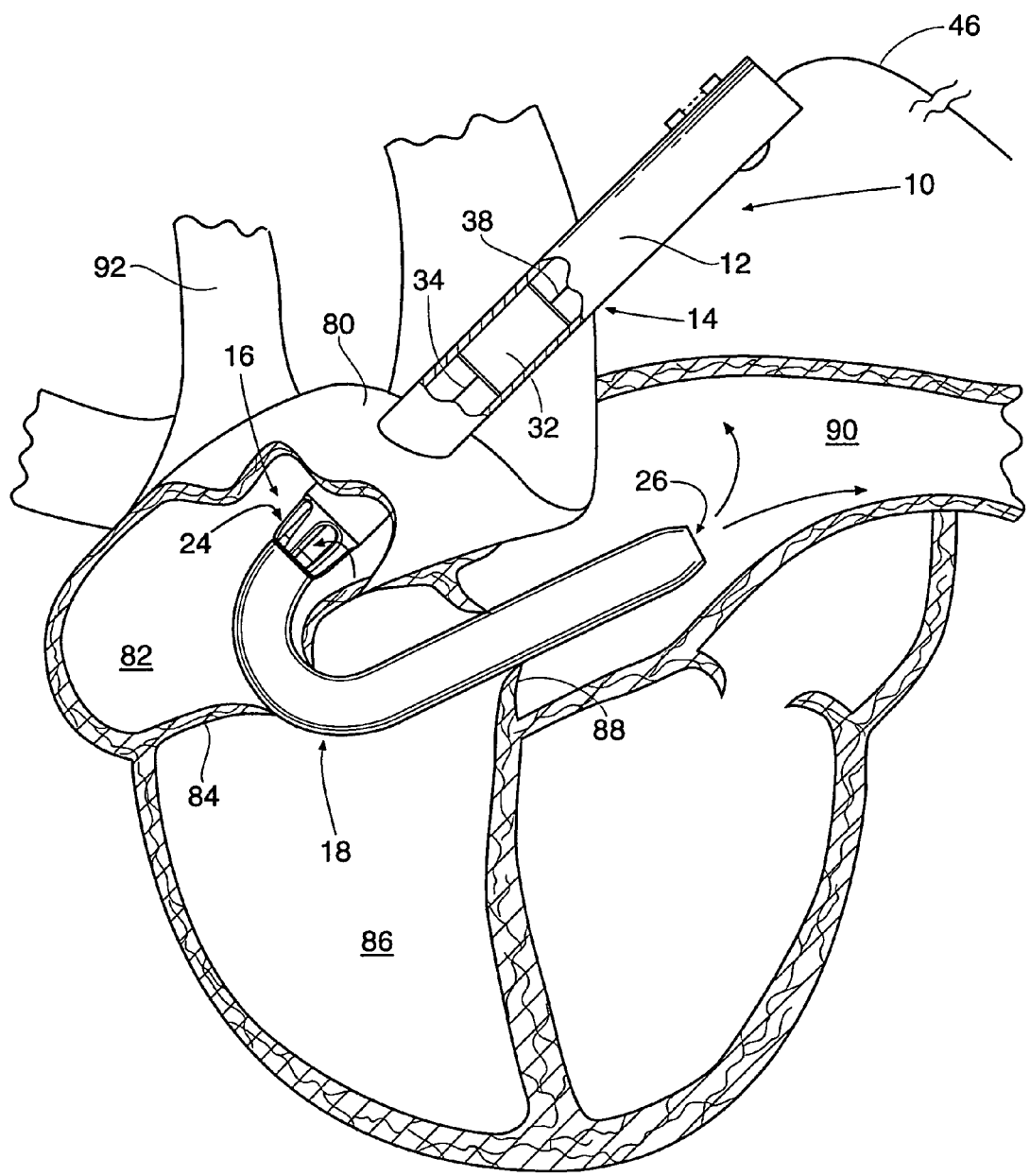
FIG. 8 is a sectional schematic view showing an integrated pump and cannula system of the present invention for providing right heart support during cardiac surgery according to the present invention.
Figure 9:
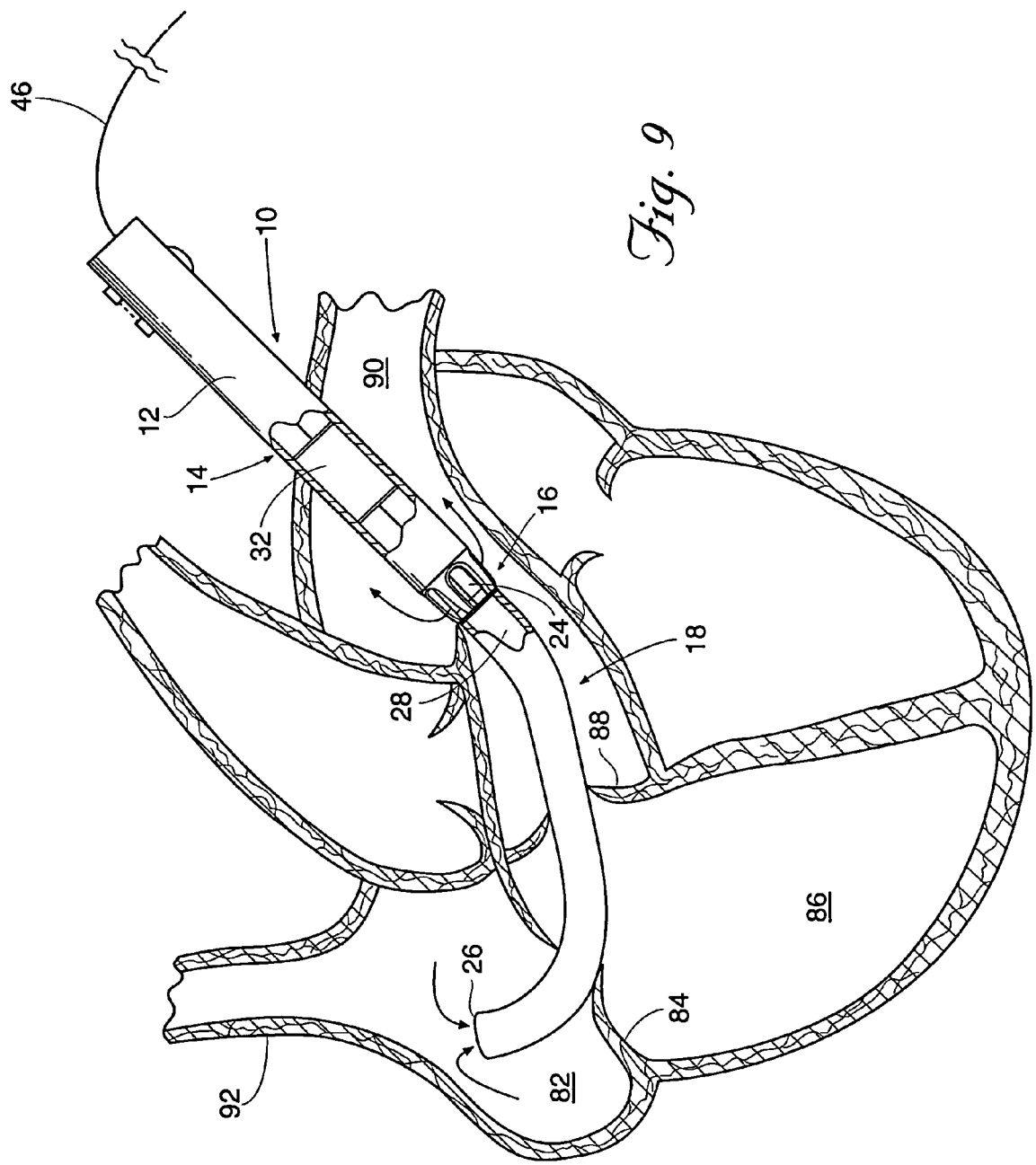
FIG. 9 is a sectional schematic view showing an integrated pump and cannula system of the present invention for providing right heart support during cardiac surgery according to the present invention.
Figure 10:
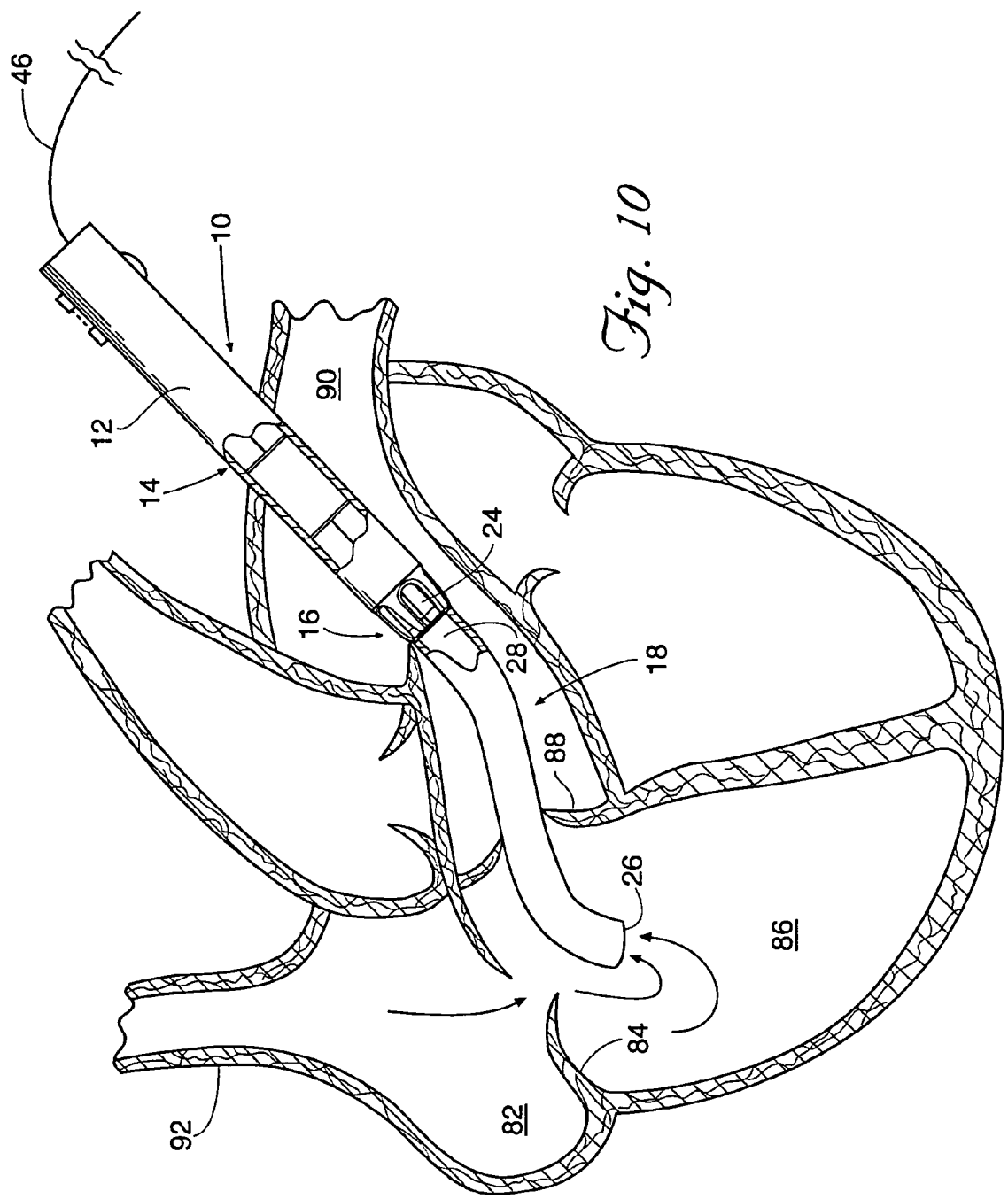
FIG. 10 is a sectional schematic view showing an integrated pump and cannula system of the present invention for providing right heart support during cardiac surgery according to the present invention.

FIGS. 8–10 illustrate exemplary embodiments of the integrated pump and cannula system 10 according to the present invention for use in providing right heart support during cardiac surgery. In FIG. 8, the cannula 12 of the integrated system of the present invention has a curved distal portion 18 that extends, in use, through the atrial appendage 80, the right atrium 82, the tricuspid valve 84, the right ventricle 86, the pulmonary valve 88, and a sufficient length and distance into the pulmonary artery 90. The pump 28 may be selectively operated (i.e. automatically or on-demand) to withdraw blood from the right atrium 82 and transport it through the flow path defined within the distal portion 18 of the cannula 12 (i.e. between flow ports 24 and flow port 26) for deposit into the pulmonary artery 90. In this fashion, blood entering the right atrium 82 may be selectively rerouted past the right ventricle 86 in an effort to supplement or replace the pumping action of the right ventricle 86 and overcome conditions where the cardiac output may become compromised, such as during cardiac surgery. The negative pressure that develops within the right atrium 82 due to the pump 28 also advantageously draws blood through or past areas of occlusion, collapse or kinking in the superior vena cava 92 and the inferior vena cava (not shown).

The pump and cannula system 10 for right heart support enables the heart to continue pumping blood in its normal fashion to provide pulmonary blood flow around cannula 12, to the extent that the heart is capable, during the lifting and manipulation of the heart during surgery. The integrated cannula and pump system 10 assures a supplemented or augmented flow of blood to the pulmonary artery 90, even in the event of compromised cardiac output, such as by disrhythmia or other interruption of pulmonary blood flow by the beating heart. Under normal circumstances, and at most times during the beating heart surgery, the internal support provided by cannula 12 will prevent the collapse of the right side of the heart and enable the heart to continue pumping at least a portion of its normal blood output into pulmonary artery 90. The combined flow of the blood flow produced by the beating heart and the blood flow produced by pump 28 and transported through the cannula 12 is at all times sufficient to sustain adequate pulmonary blood flow to sustain the patient during surgery. In the event of a disrhythmia, the pump 28 can be increased in output to compensate until the disrhythmia is corrected. The pump and cannula system 10 can thus overcome any compromise in right heart function or output during beating heart surgery (such as collapse or kinking that may occur in the vena cava 92, right atrium 82, right-ventricle 86, and/or pulmonary artery 90 when the heart is lifted or manipulated) and thus avoid the need for CPB.

The cannula 12 is preferably sealed within the incision formed in the wall of atrial appendage 80 through the use of a purse-string suture, as well known in the art, or any other suitable sealing mechanisms. The length into which the cannula 12 extends past the pulmonary valve 88 into pulmonary artery 90 will depend on the beating heart surgical procedure being performed and on other factors. In general, the cannula 12 should extend through and past an area defined generally as the "kink zone," which will vary in size and location depending on condition of the patient, the surgical procedure performed and the extent of movement and manipulation of the heart during surgery. The kink zone will frequently extend up to the point where the pulmonary artery is not moved during surgery. It is generally expected that the cannula 12 will need to extend up to about 15 cm beyond pulmonary valve 88 and into pulmonary artery 90. Such a length is generally sufficient to prevent kinking or collapsing of pulmonary artery 90 during the positioning of the heart for beating heart bypass surgery. Preferably, the length beyond the pulmonary valve 88 will generally be up to about 10 cm, or preferably up to about 7 cm, or about 4 cm but may be as little as about 1 cm depending on the kind and size of cannula used.

FIG. 9 illustrates the integrated pump and cannula system 10 according to the present invention for providing right heart support during cardiac surgery via retrograde pumping. In this embodiment, the main body 14 of the cannula 12 extends through the wall of the pulmonary artery 90, the intermediate portion 16 is disposed in the pulmonary artery 90, and the distal portion 18 extends, in use, through the pulmonary artery 90, the pulmonary valve 88, the right ventricle 86, and through the tricuspid valve 84 for deposit into the right atrium 82. Pump 28 may be selectively operated (i.e. automatically or on-demand) to withdraw blood from the right atrium 82, and through the flow path defined within the distal portion 18 of the cannula 12 for deposit into the pulmonary artery 90. Referring to FIG. 10, the distal portion 18 of the cannula 12 may be curved and/or positioned so that the flow port 26 thereof is disposed within the right ventricle 86 instead of the right atrium 82. Blood within the right ventricle 86 may thus be selectively transported through the pulmonary valve 88 and into the pulmonary artery 90 to supplement or replace the pumping action of the right ventricle and overcome conditions where the cardiac output of the right heart may become compromised during beating heart surgery, such as collapse or kinking that may occur in the vena cava 32, right atrium 82, right ventricle 86, and/or pulmonary artery 90 when the heart is lifted or manipulated to provide surgical access to lateral or posterior heart vessels.

Figure 11:
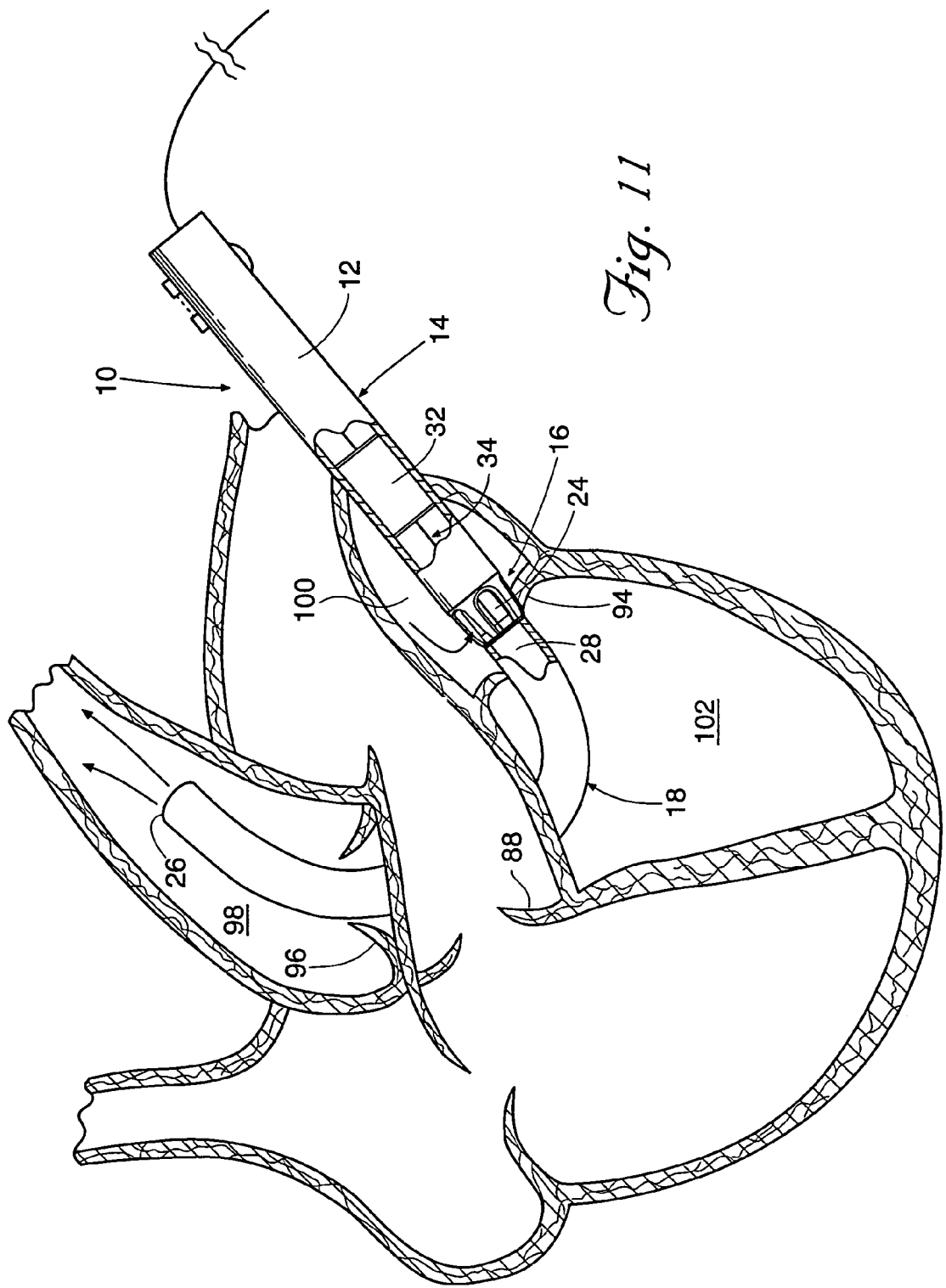
FIG. 11 is a sectional schematic view showing an integrated pump and cannula system of the present invention for providing left heart support during cardiac surgery according to the present invention.
Figure 12:
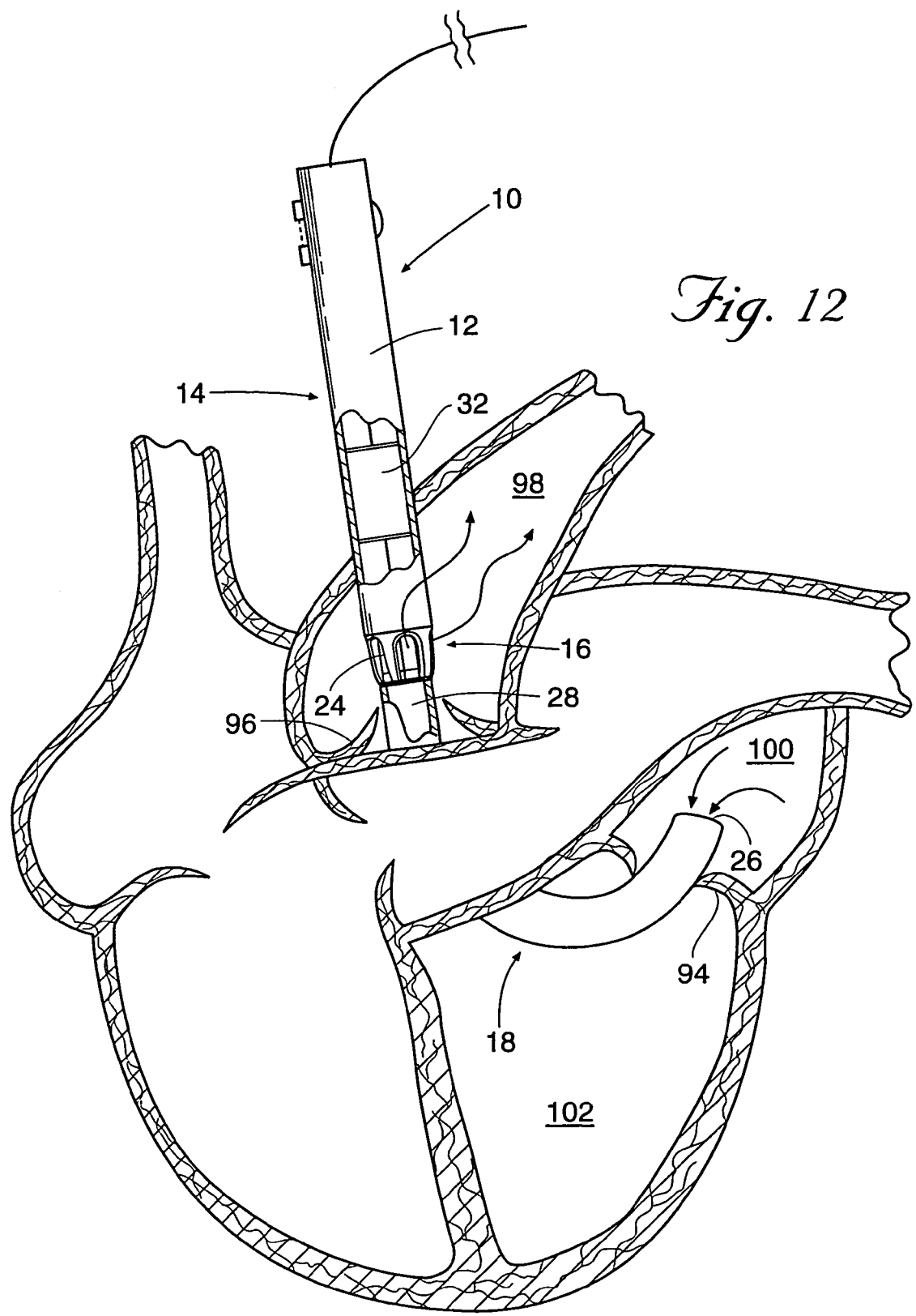
FIG. 12 is a sectional schematic view showing an integrated pump and cannula system of the present invention for providing left heart support during cardiac surgery according to the present invention.
Figure 13:
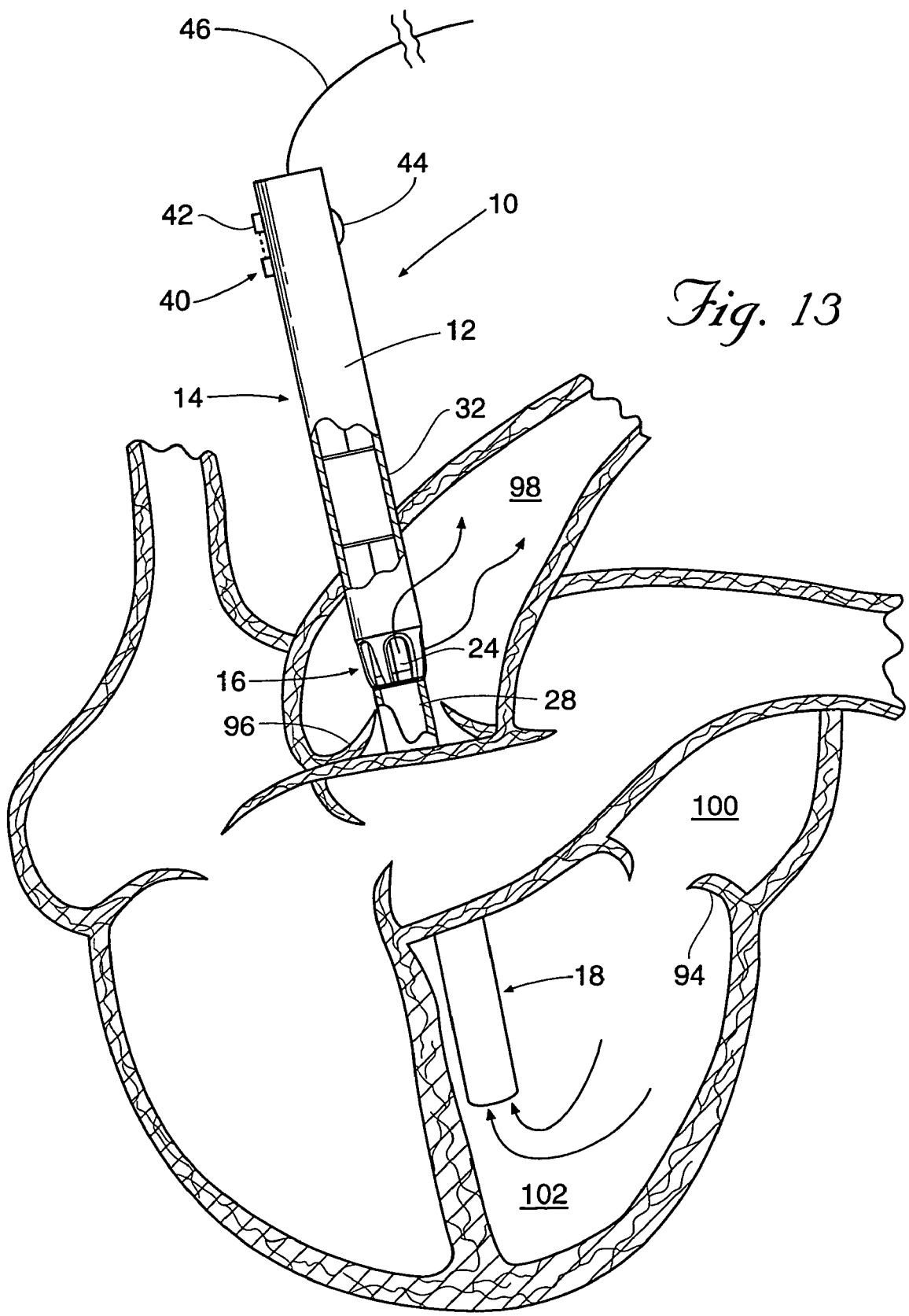
FIG. 13 is a sectional schematic view showing an integrated pump and cannula system of the present invention for providing left heart support during cardiac surgery according to the present invention.

FIGS. 11–13 illustrate exemplary embodiments of the integrated pump and cannula system 10 according to the present invention for use in providing left heart support during cardiac surgery. In FIG. 11, the cannula 12 of the integrated system of the present invention has a curved distal portion 18 that extends, in use, through the bicuspid valve 94, through the aortic valve 48, and a sufficient length into the aorta 98. The main body portion 14 of the cannula 12 is positioned through the wall of the left atrium 100 such that the flow ports 24 are disposed within the left atrium 100 and the flow port 26 is disposed within the aorta 98. The pump 28 may be selectively operated (i.e. automatically or on-demand) to withdraw blood from the left atrium 100, through the flow ports 24, and through the fluid path defined within the distal portion 18 of the cannula 12 for delivery out the flow port 26 into the aorta 98. This establishes a protected blood flow path within the left atrium 100, left ventricle 102, and aorta 98 such that, under the direction of the pump 28, the aortic or circulatory blood flow from the heart may be selectively augmented during cardiac surgery, thereby avoiding the need for CPB. FIG. 12 discloses the pump and cannula system 10 employed in a reverse fashion, wherein the main body portion 14 is introduced into the heart via the wall of the aorta 98 such that the flow ports 24 are disposed in the aorta 98 and the flow port 26 is disposed in the left atrium 100. FIG. 13 shows another alternate embodiment of the integrated pump and cannula system 10shown in FIG. 12, the only difference being that the distal portion 18 of the cannula 12 is not curved such that, upon entry into the wall of the aorta 98, the flow port 26 is disposed within the left ventricle 102. The operation of pump 28 in either embodiment provides left heart assists by transporting blood from upstream of the aortic valve 96 and/or bicuspid valve 94. In all embodiments, protected blood flow paths are thus established within some or all of the left heart to maintain at least partial blood flow at all time. The integrated pump and cannula system 10 is thus capable of overcoming any compromise in left heart function or output during beating heart surgery, such as collapse or kinking that may occur in the left atrium 100, left ventricle 102, and/or aorta 98 when the heart is lifted or manipulated to provide surgical access to lateral or posterior heart vessels.

One advantage of using the integrated pump and cannula system 10 for right and/or left heart support is that it allows the beating heart to continue to pump whatever blood it is capable of pumping under the conditions of the beating heart surgery. When the right and/or left side(s) of the heart is supported according to this invention to establish a protected blood flow path therein (thus preventing collapse, kinking, or occlusion of the right and/or left sides), the beating heart can provide substantial, if not full or sufficient, pulmonary and/or circulatory blood flow during the beating heart surgery. In an important aspect, the pump and cannula system 10 may be employed in either or both sides of the heart to avoid the need for CPB in such cardiac procedures.

Figure 14:
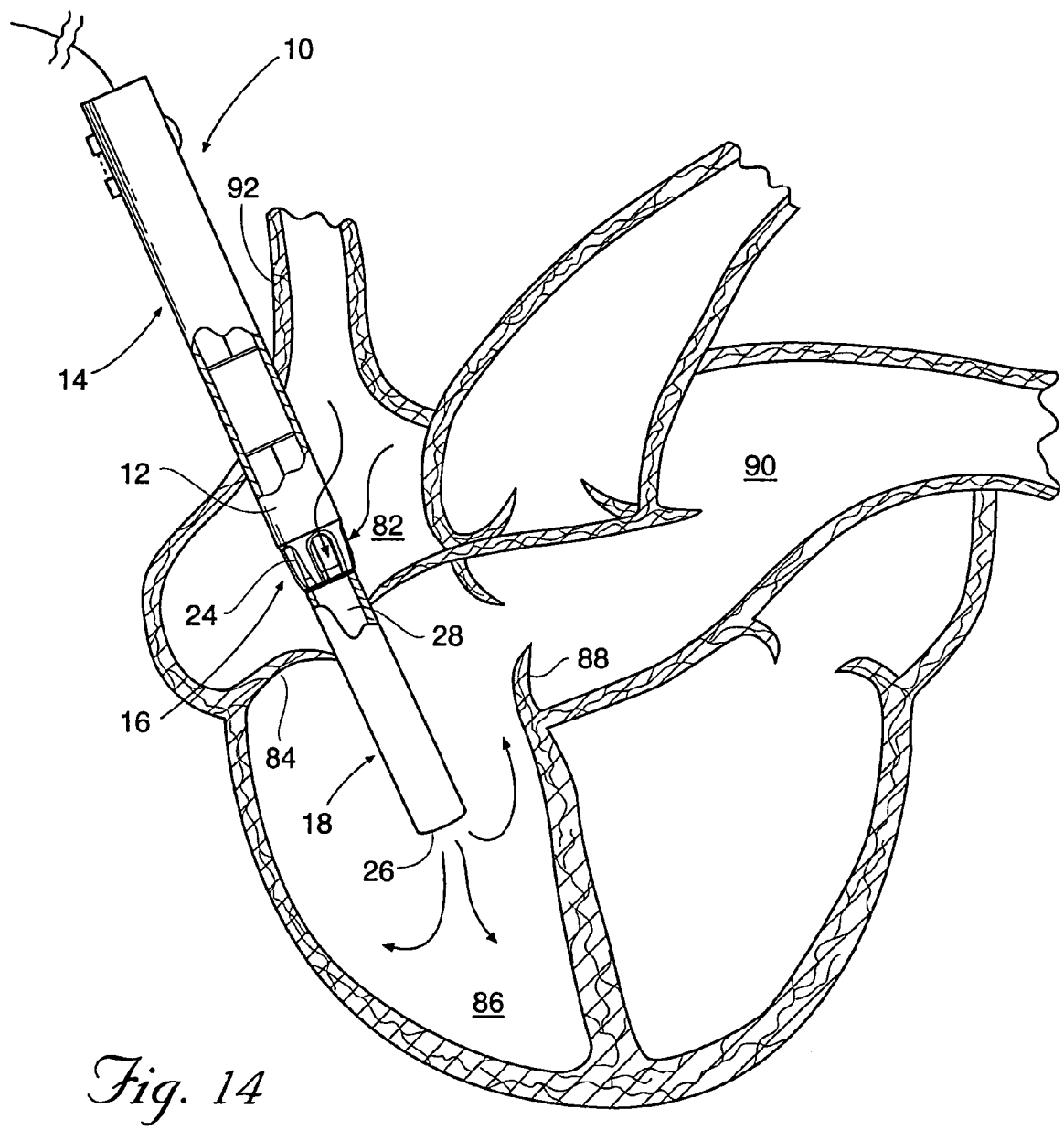
FIG. 14 is a sectional schematic view showing an integrated pump and cannula system of the present invention for preloading the right ventricle according to the present invention.
Figure 15:
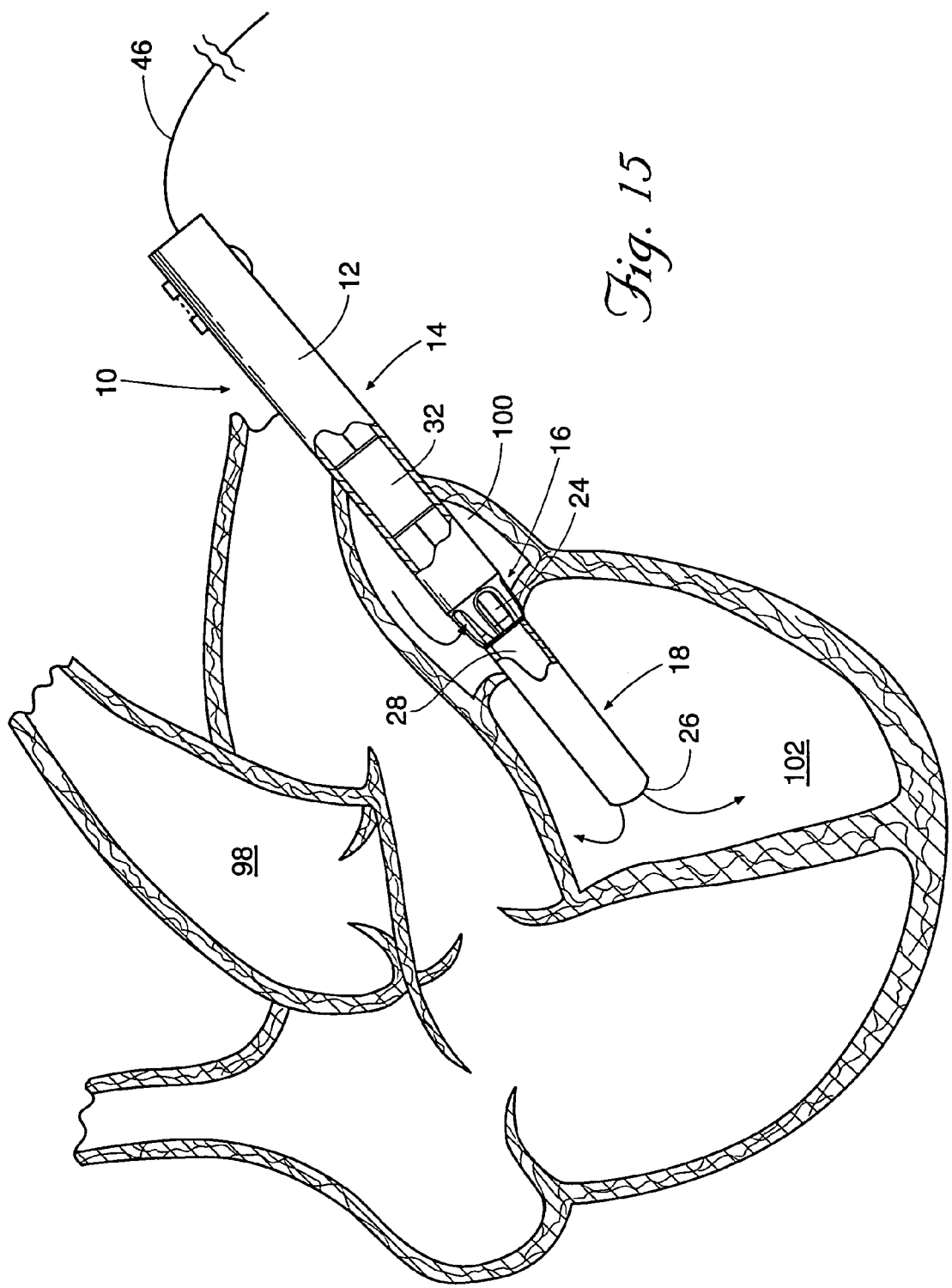
FIG. 15 is a sectional schematic view showing an integrated pump and cannula system of the present invention for preloading the left ventricle according to the present invention.

FIGS. 14–15 illustrate another advantageous application ("ventricular preloading") of the integrated pump and cannula system 10 of the present invention. FIG. 14 illustrates the integrated pump and cannula system 10 configured and positioned within the heart to provide right ventricular preloading. FIG. 15 illustrates the integrated pump and cannula system 10 configured and positioned within the heart to provide left ventricular preloading. The pump and cannula 12 has been described and shown above for providing right and/or left heart support wherein blood is deliberately re-routed through and past the right and/or left ventricle in an effort to reduce the volume of blood to be pumped by the particular ventricle. While "unloading" the ventricles in this fashion is preferred in certain instances, it is to be readily understood that the pump and cannula arrangements described herein may also be employed to "preload" the ventricles. Ventricular preloading may be accomplished by positioning the outflow cannula from the pump into a given ventricle such that the pump may be employed to fill or preload the ventricle with blood. This may be particularly useful with the right ventricle, as shown in FIG. 14, where the integrated pump and cannula system 10 is positioned such that the flow ports 24 are disposed in the right atrium 82 and the flow port 26 is disposed in the right ventricle 86. On occasion, the right ventricle is not supplied with sufficient levels of blood from the right atrium 82 such that, upon contraction, the right ventricle 86 delivers an insufficient quantity of blood to the pulmonary artery 90. This may result when the right ventricle and/or right atrium are in a stressed or distorted condition during surgery. Preloading overcomes this problem by actively supplying blood into the right ventricle 86, thereby facilitating the delivery of blood into the pulmonary artery. With reference to FIG. 15, this same technique can be used to preload the left ventricle 102 and thus facilitate the delivery of blood from the left ventricle 102 into the aorta 98.

Figure 16:
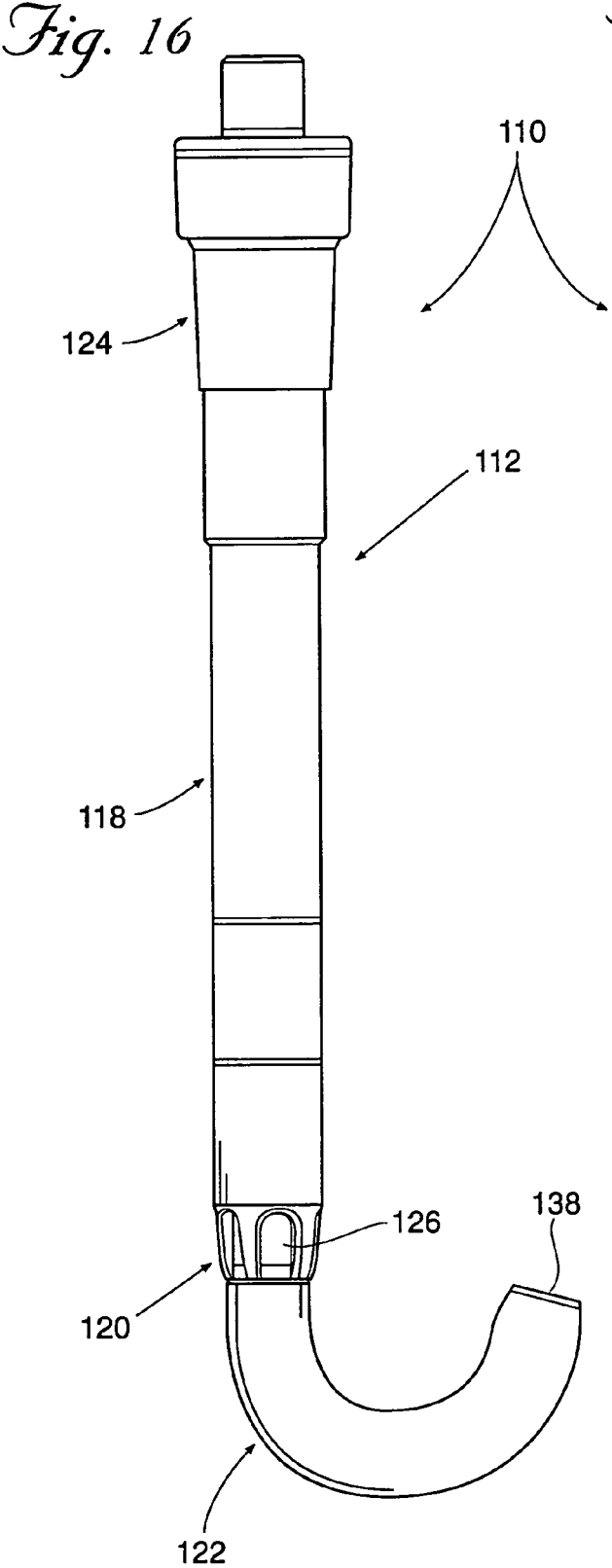
FIG. 16 is a side view showing an outer cannula forming part of a dual cannula integrated pump and cannula system of the present invention.
Figure 17:
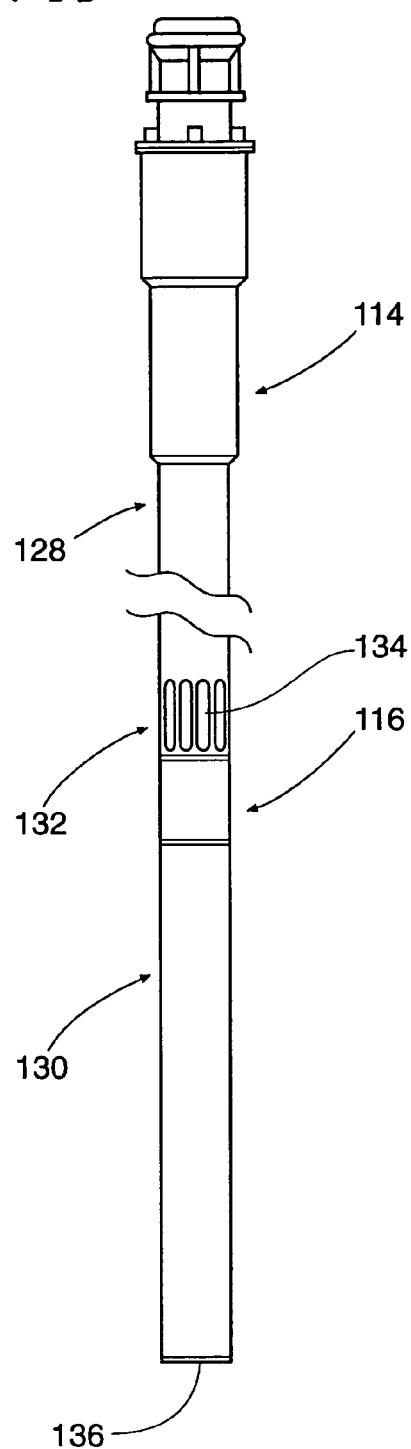
FIG. 17 is a side view showing an inner cannula and pump arrangement forming part of a dual cannula integrated pump and cannula system of the present invention.

FIGS. 16 and 17 illustrate an integrated pump and cannula assembly 110 having a dual lumen configuration according to the present invention. In this embodiment, the integrated pump and cannula system 110 includes an outer cannula 112 (FIG. 16) and an inner cannula 114 having an internally disposed blood pump 116 (FIG. 17). The outer cannula 112 is generally of the type shown and described in commonly-assigned and copending Int'l Patent App. Ser. No. PCT/US99/13666, filed 18 Jun. 1999, and the inner cannula 114 and pump 116 are generally of the type shown and described in commonly-assigned and copending U.S. Provisional Patent App. Ser. No. 60/152,249, filed Sep. 3, 1999, the contents of which are hereby incorporated herein by reference.

The outer cannula 112 includes a main body portion 118, an intermediate portion 120, and a curved distal portion 122. The main body portion 118, intermediate portion 120 and curved distal portion 122 defined a single continuous lumen extending the entire length of the outer cannula 112. As with the intermediate portion 16 described above, a plurality of apertures defining flow ports 126 are formed in the intermediate portion 120 of the outer cannula 112. The outer cannula 112 has a connector 124 having an internally disposed hemostasis valve (not shown) which is adapted to slideably receive the inner cannula 114 therethrough while preventing the unwanted introduction of air into the outer cannula 112 and leakage of fluids from the outer cannula 112. In practice, the outer cannula 112 is introduced into the heart, and the inner cannula 114 is thereafter introduced through the outer cannula 112 such that the pump 116 is disposed and maintained in position within the curved distal portion 122 of the outer cannula 112.

Figure 19:
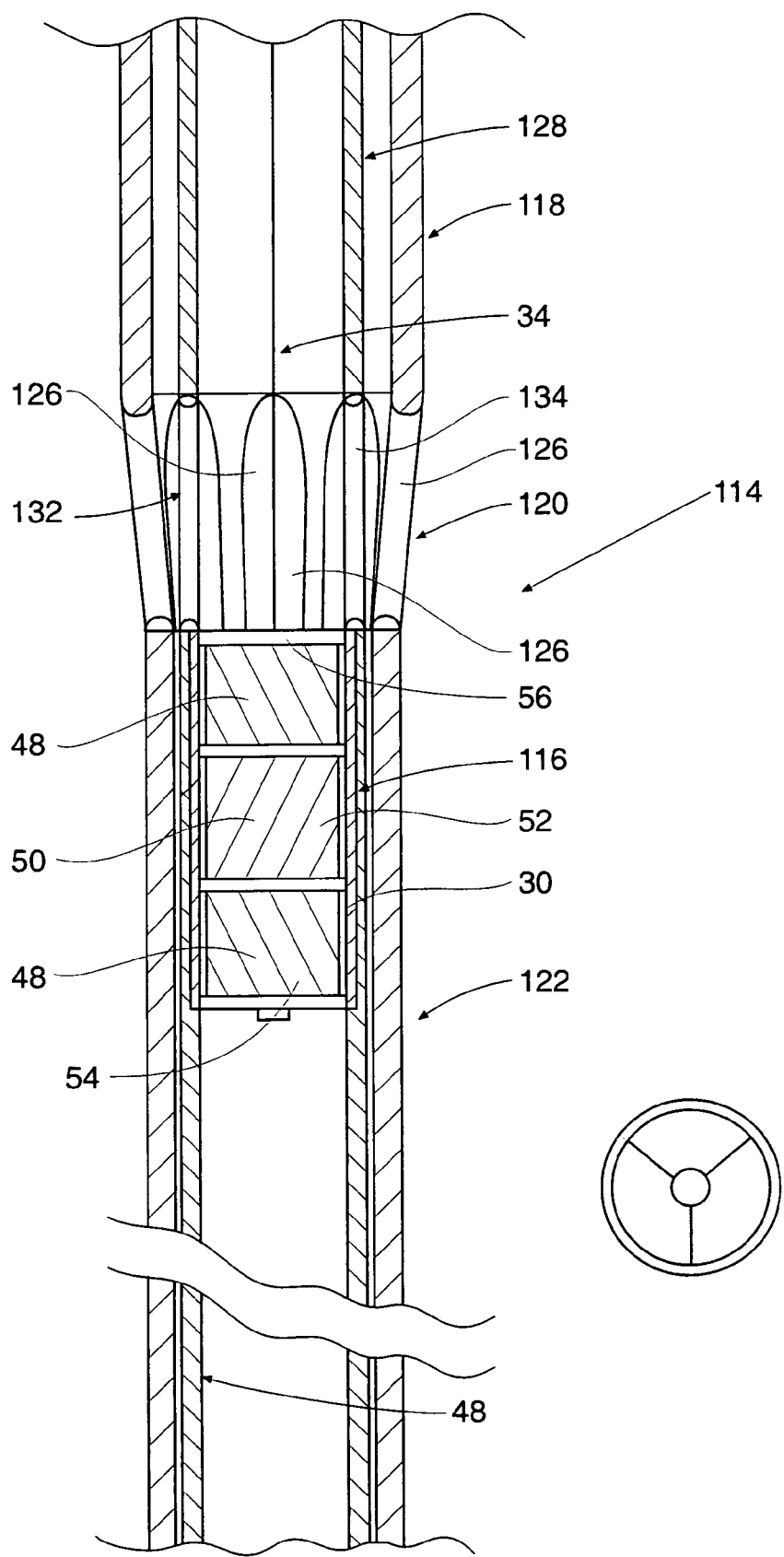
FIG. 19 is a sectional side view illustrating the construction of the pump and portions of the cannula of the integrated pump and cannula system shown in FIG. 18.

The inner cannula 114 includes a proximal portion 128 and a distal portion 130 extending on either side of an intermediate portion 132 having flow ports 134 formed therein. The pump 116 disposed within the inner cannula 114 may be of the same construction and operation as the pump 28 described above. As will be described in greater detail below, a drive shaft (not shown) extends from the rotor (not shown) disposed within the pump 116, through the intermediate and proximal portions 132, 128, for connection to a motor (not shown). The inner cannula 114 is dimensioned to be inserted into the outer cannula 112 such that the flow port 136 in the distal end of the distal portion 130 extends, in use, through and past an aperture 138 formed in the distal end of the curved distal portion 122. As shown in FIG. 19, the pump 116 will preferably be positioned such that the flow ports 134 are generally aligned with the flow ports 126 of the outer cannula 112. The pump 116 may then be selectively driven to transport fluid (i.e. blood) through the flow path defined between the flow ports 126, 136. The inner cannula 114 may be provided at its proximal end with a connector suitably sized to interface with any of controller and/or pumping arrangements. The length of the outer cannula 112 and the inner cannula 114 is application specific. In a CABG application, for example, the pulmonary artery is a destination into which blood may be returned into the patient from the pump system via the inner cannula 114, and the dimensions of the inner cannula 114 are selected accordingly.

Figure 18:
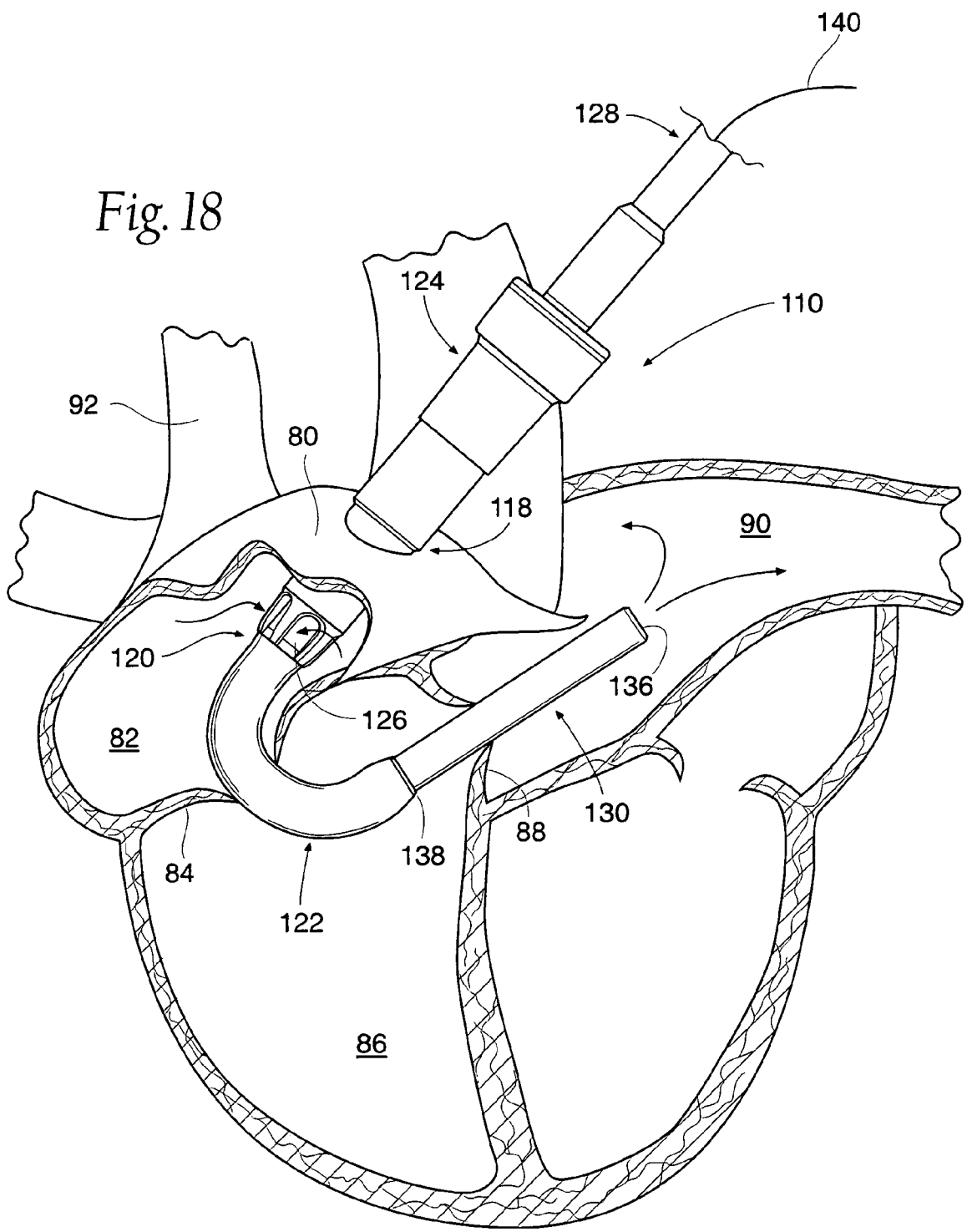
FIG. 18 is a sectional schematic view showing an dual cannula integrated pump and cannula system of the present invention for providing right heart support during cardiac surgery according to the present invention.

FIG. 18 illustrates the integrated pump and cannula assembly 110 of this embodiment supporting the right side of the heart during cardiac surgery. The outer cannula 12 is adapted to be introduced into the heart through the atrial appendage 80. A sheathed power cable or drive shaft 140 may be extended through the inner cannula 114 depending upon whether the motor (not shown) for driving the pump 116 is disposed within the dual cannula assembly 110 or located external to the dual cannula assembly 110. In some embodiments, the inner cannula 114 may be positioned entirely within the outer cannula 112, in which case the hemostasis valve will seal around the sheathed power cable or drive shaft 140. In either event, the hemostasis valve within the connector 124 reduces the possibility of blood leakage or emboli forming within the patient's blood stream. The inner cannula 114 and outer cannula 112 combine to provide a protected blood flow path within the right side of the heart. Under the direction of the pump 116, blood from within the right atrium 82 may be selectively transported directly through the inner cannula 114 into the pulmonary artery 90. In this fashion, the pump and cannula system 110 may be utilized to provide right heart support to overcome any of the above-identified compromise conditions in cardiac output that may occur during beating heart surgery to avoid the need for CPB.

Figure 20:
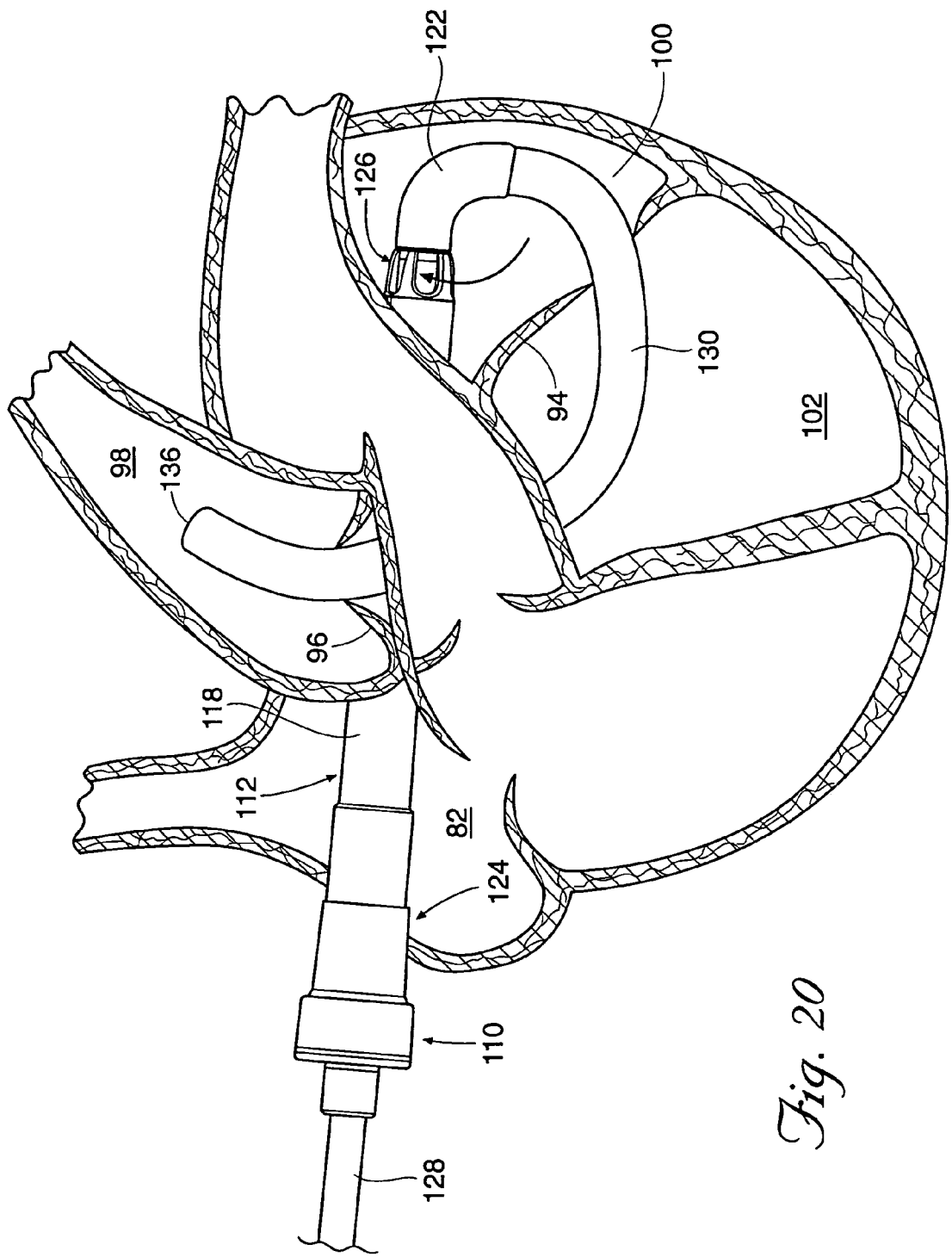
FIG. 20 is a sectional schematic view showing an dual cannula integrated pump and cannula system of the present invention piercing the atrial wall for providing left heart support during cardiac surgery according to the present invention.

FIG. 20 discloses yet another use of the dual cannula integrated pump and cannula system 110. In this embodiment, the outer cannula 112 is introduced into the heart (through the right atrium 82) such that it pierces the atrial septum to position the flow ports 126 of the outer cannula 112 (and the flow ports 124 of the inner cannula 114) within the left atrium 100. The inner cannula 114 is further configured to extend through the bicuspid valve 94, the left ventricle 102, and into the aorta 98. This integrated pump and cannula system 110 is capable of re-routing blood from the left atrium to the aorta to bypass the left ventricle to provide left heart support, thereby overcoming compromise conditions that may otherwise require the use of CPB. Optional balloons (not shown) may also be provided on the cannula 114 such that, when positioned in the heart, the inflatable balloons may be positioned on either side of a heart valve (such as the aortic valve 96) to cut off the blood flow therethrough, such as may be advantageous in valve repair procedures.

The pump arrangements disclosed herein may be operator-regulated as discussed above with regard to the control circuit 40 disposed on the integrated pump and cannula system 10 shown in FIGS. 1–15. The pumps may also be regulated automatically through the use of a controller for each pump or a controller to control all pumps in a particular system if more than one integrated pump and cannula assembly according to the present invention are combined. In one embodiment, pump speed and output may be controlled based on the measurement of a pressure transducer disposed at the arterial blood flow area to measure pulmonary artery blood pressure and aorta blood pressure. The central venous pressure can also be used separately or with the pulmonic and/or aortic pressure. The selected blood pressure measurement can provide the basis for a manual or automatic control of the individual and separate pump speeds and outputs. The desired or target pulmonary and aortic blood pressures can be determined by the surgical team for each patient depending on condition of the patient and surgical procedure being performed. The desired or target pressures may change or be different for different stages of the surgical procedure. In general, a desired pressure range is about 20–30 mmHg, although pressures as low as about 10–15 mmHg may be acceptable for limited periods of time. The controller can operate in response to one selected pressure or can operate in response to other parameters. It is further preferred that the controller and the control system incorporate other input data, in addition to arterial pressure, such as blood pressure elsewhere in the body, blood oxygen level, actual blood flow volume, blood C02 level, etc. A desired automatic control criteria is where a control loop for each pump is established whereby a target total blood flow is maintained by the sum of any beating heart blood flow output plus the pump flow output. Thus, the patient is assured of adequate pulmonary and circulatory blood flow throughout the surgery regardless of the output of the heart, without any CPB machine use. The pulmonary artery pressure and pulmonary blood flow rates will need to be adjusted accordingly when only one lung is being used during the surgery, and the aortic circulatory blood flow may also have to be adjusted in such mode of operation. The pump and cannula systems of this invention can provide 0–100% of the required blood flow to sustain the patient with the heart providing 100–0% of the blood flow. When the pump system is providing part of the blood flow in a beating heart procedure, the pump can provide about 10, 20, 30, 40, 50, 60, 70, 80, or 90% of the total blood flow for the side of the heart in question with the beating heart providing the remainder of the blood flow needed to sustain the patient during the surgery.

The integrated pump and cannula of the present invention has been discussed above largely with reference to beating heart surgery. However, as mentioned above, the system of the present invention finds applicability in a wide range of other surgical procedures, such as still or stopped heart surgery. In these procedures, after the pump is activated, medication or drugs for slowing or completely stopping the heart may be administered when used to support cardiac functions. The pumping rate of the pump may be adjusted to maintain sufficient circulation or to accommodate changes in circulatory demand. The pump may also be equipped with sensing devices (not shown) for measuring various body conditions such as blood pressure, the presence of blood, blood oxygen content, or other parameters that would suggest the need for altering the flow rate of the integrated pump and cannula system. For example, the apparatus may include pressure sensors along the cannula(s) so that a present pressure change would signal the need to change the pumping capacity of the apparatus. The pump may also include sensors to sense the pressure at the distal end of pump and cannula system so that a present pressure change could signal the need to change the pumping capacity of the pump, also the pressure change could be used to signal to the operator the location of the distal end of the cannulas. When the pressure at the proximal ports of the cannula decreases by a certain increment, which indicates commencement of pump suction, a controller used with the apparatus may provide warning signals or automatically decrease the flow rate of the apparatus until returning to a preset pressure within the main lumen of the integrated pump and cannula system. In the removal of the fluid transport device, the insertion wound may be restored using common surgical techniques.

Figure 21:
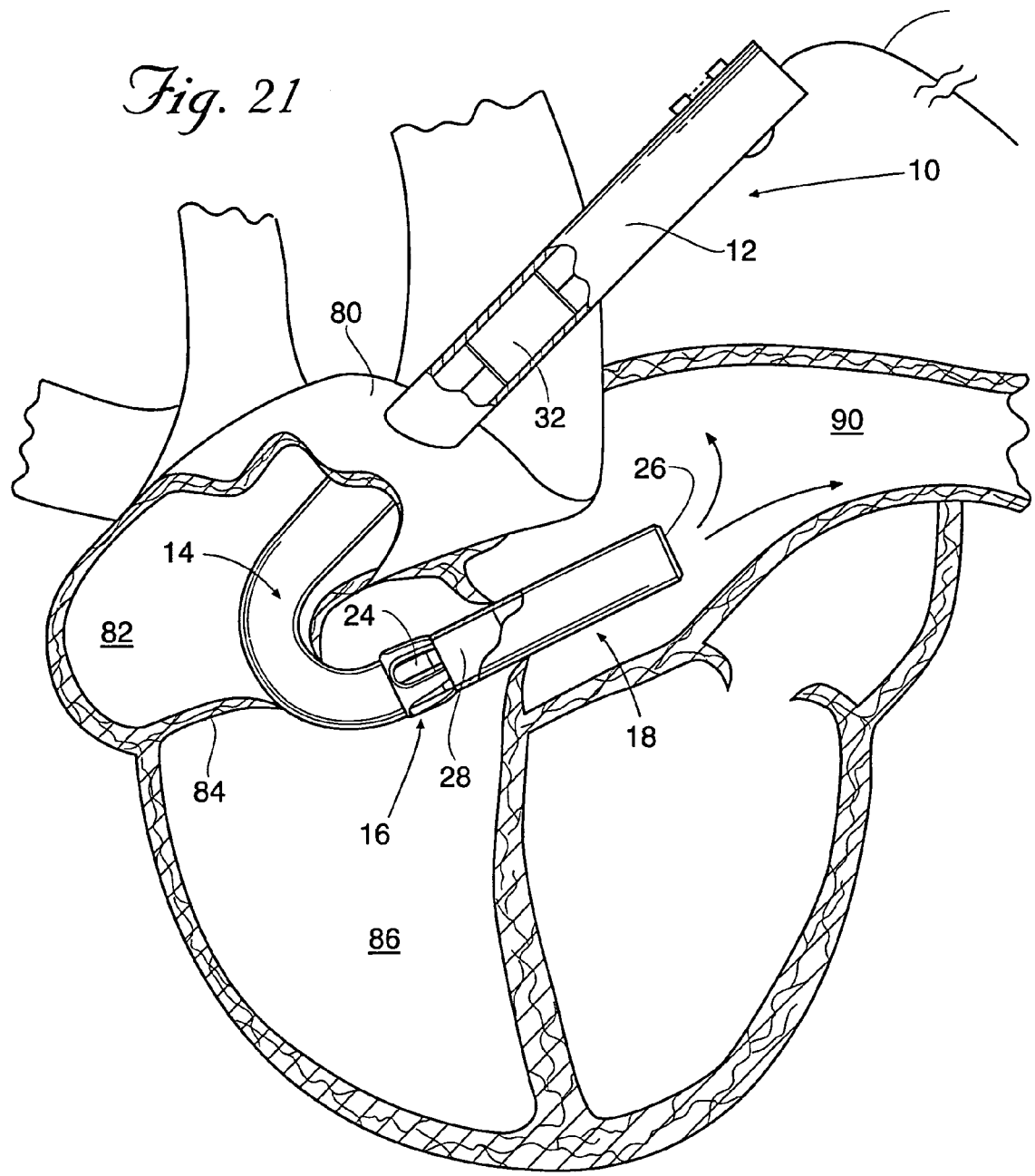
FIG. 21 is a sectional schematic view showing an integrated pump and cannula system of the present invention for providing right heart support during cardiac surgery according to the present invention.
Figure 22:
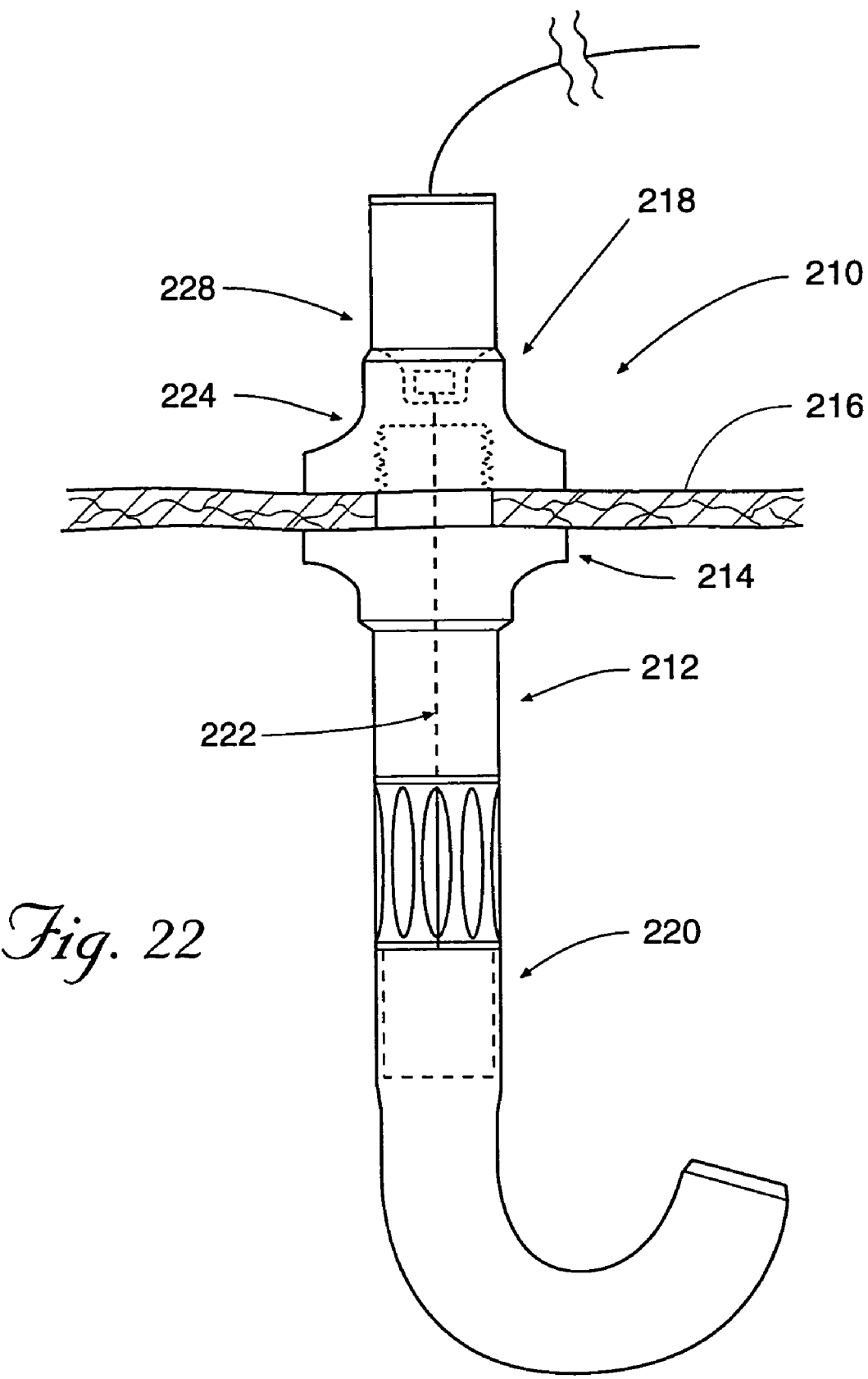
FIG. 22 is a sectional schematic view illustrating an integrated pump and cannula system of the present invention for providing right heart support during cardiac surgery according to the present invention.

It is to be readily appreciated that the foregoing pump and cannula systems are presented by way of example, and that any number of alternate cannula configurations and designs may be employed without departing from the scope of the present invention. For example, FIG. 21 illustrates the integrated pump and cannula system 10 of the present invention wherein the main body portion 14 of the cannula 12 is curved such that the flow ports 24 are positioned within the right ventricle 86 and the distal portion 18 extends straight into the pulmonary artery 90. In another embodiment of the present invention shown in FIG. 22, an integrated pump and cannula system 210 may be provided comprising a cannula 212 extending distally from a connector member 214 designed to extend through a tissue wall 216 (i.e. wall of right atrium 82) for connection to an external drive unit 218. A pump 220 is disposed within the cannula 212, which is coupled to the drive unit 218 via a solid drive shaft 222 which extends from the rotor (not shown), through the lumen within the cannula 212, and outward through a connector 224 (threadably secured to an extending portion 226 of the connector 214) for connection to a drive coupler or motor assembly 228. Moreover, while many of the pumps disclosed above are axial flow pumps, it is to be readily understood that the pumps may also comprise mixed-flow intravascular pumps, particularly when employed within the cannula system of the present invention to transport blood within the heart in a retrograde fashion.

The integrated pump and cannula system of the present invention advantageously provides the ability to transport fluids between different locations within a body in a wide variety of applications, most particularly in enabling various types of heart surgery procedures to be performed without the use of CPB machines by maintaining sufficient pulmonary blood flow through the patient's lungs (or lung) and sufficient circulatory blood flow through the patient's body to sustain the patient during the surgery.

What is claimed is:

1. A system for maintaining at least partial blood flow within a heart, comprising:
   a conduit having an inner flow path and an outer flow path, the conduit being sized and configured to be introduced into the heart through at least one of the wall of the right atrium, the wall of the right ventricle, the wall of the pulmonary artery, the wall of left atrium, the wall of the left ventricle, and the wall of the aorta;
   said conduit including a blood inlet port communicating with one of the inner flow path and the outer flow path and a blood outlet port communicating with the other one of the inner flow path and the outer flow path, said blood inlet port and said blood outlet port being sized and configured to be positioned on either side of at least one of the tricuspid valve, the pulmonary valve, the bicuspid valve, and the aortic valve; and
   a blood pump disposed within said conduit for selectively transporting blood from said blood inlet port to said blood outlet port of said conduit.

2. The system of claim 1, wherein said conduit is sized and configured to be positioned within the heart such that said blood inlet port is disposed within the right atrium, said blood outlet is positioned in the pulmonary artery, and wherein said pump may be selectively operated to maintain at least partial blood flow through the protected blood flow path established within the conduit.

3. The system of claim 1, wherein said conduit is sized and configured to be positioned within the heart such that said blood inlet port is disposed within the left atrium, said blood outlet is positioned in one of the left ventricle and the aorta, and wherein said pump may be selectively operated to maintain at least partial blood flow through the protected blood flow path established within the conduit.

4. The system of claim 1, wherein said conduit is sized and configured to be positioned within the heart such that said blood inlet port is disposed within the pulmonary artery, said blood outlet is positioned in one of the right ventricle and right atrium, and wherein said pump may be selectively operated to maintain at least partial blood flow through the protected blood flow path established within the conduit.

5. The system of claim 1, wherein said conduit is sized and configured to be positioned within the heart such that said blood inlet port is disposed within the right atrium, said blood outlet is positioned in the right ventricle, and wherein said pump may be selectively operated to maintain at least partial blood flow through the protected blood flow path established within the conduit.

6. The system of claim 1, wherein said conduit is sized and configured to be positioned within the heart such that said blood inlet port is disposed within the left atrium, said blood outlet is positioned in the left ventricle, and wherein said pump may be selectively operated to maintain at least partial blood flow through the protected blood flow path established within the conduit.

7. The system of claim 1, wherein said pump is one of an axial flow blood pump and a mixed flow blood pump disposed within the conduit for transporting blood from said blood inlet to said blood outlet.

8. The system of claim 1, further including
   a control circuit forming part of said conduit to allow a user to manually or automatically control the speed and rotation of said pump.

9. The system of claim 1, wherein said conduit includes at least one pre-formed curve along its length.

* * * * *